United States Patent
Mitra et al.

(10) Patent No.: US 11,542,495 B2
(45) Date of Patent: Jan. 3, 2023

(54) PREPARATIVE ELECTROPHORETIC METHOD FOR TARGETED PURIFICATION OF GENOMIC DNA FRAGMENTS

(71) Applicants: Sage Science, Inc., Beverly, MA (US); Washington University, St. Louis, MO (US)

(72) Inventors: Robi David Mitra, Fenton, MO (US); Jeffrey Milbrandt, St. Louis, MO (US); Ezra Solomon Abrams, Newton, MA (US); Todd J. Barbera, Marblehead, MA (US); T. Christian Boles, Bedford, MA (US)

(73) Assignees: Sage Science, Inc., Beverly, MA (US); Washington University, St. Louis, MO (US)

( * ) Notice: Subject to any disclaimer, the term of this patent is extended or adjusted under 35 U.S.C. 154(b) by 669 days.

(21) Appl. No.: 15/777,577

(22) PCT Filed: Nov. 21, 2016

(86) PCT No.: PCT/US2016/063190
§ 371 (c)(1),
(2) Date: May 18, 2018

(87) PCT Pub. No.: WO2017/087979
PCT Pub. Date: May 26, 2017

(65) Prior Publication Data
US 2021/0207122 A1 Jul. 8, 2021

Related U.S. Application Data

(60) Provisional application No. 62/258,384, filed on Nov. 20, 2015.

(51) Int. Cl.
*C12N 15/10* (2006.01)
*G01N 27/447* (2006.01)

(52) U.S. Cl.
CPC ..... *C12N 15/101* (2013.01); *G01N 27/44747* (2013.01)

(58) Field of Classification Search
None
See application file for complete search history.

(56) References Cited

U.S. PATENT DOCUMENTS 3,407,133 A 10/1968 Oliva et al.
3,533,933 A 10/1970 Strauch
(Continued)

FOREIGN PATENT DOCUMENTS

CN 101024851 A 8/2007
CN 101907532 A 12/2010
(Continued)

OTHER PUBLICATIONS

T.F. O'Sullivan, et al., "Comparison of Streptococcus thermophilus strains by pulsed field gel electrophoresis of genomic DNA", FEMS Microbiology Letters, 168(2):p. 213-219, (Nov. 1998).*
(Continued)

*Primary Examiner* — J. Christopher Ball
(74) *Attorney, Agent, or Firm* — Cooley LLP

(57) ABSTRACT

A sample containing particles having high-molecular-weight (HMW) DNA is entrapped in a gel matrix, and the gel matrix is exposed to a lysis reagent configured to release the HMW DNA from the particles. The HMW DNA may be purified by subjecting the gel matrix to an electrophoretic field that removes the HMW DNA from the particles, lysis reagents, and/or other sample constituents, from the gel matrix such that the HMW DNA remains. The gel matrix may be subjected with DNA cleavase reagents configured to cleave at specific DNA sequences within the HMW DNA to liberate defined segments of the DNA as fragments of reduced size. The gel matrix may also be subjected to an electrophoretic (Continued)

field, which moves and separates the DNA fragments from uncleaved DNA of the HMW DNA, which remains substantially immobile. The electrophoretically separated DNA fragments may be isolated from the gel matrix.

12 Claims, 4 Drawing Sheets

Specification includes a Sequence Listing.

(56) References Cited

U.S. PATENT DOCUMENTS

| | | | |
|---|---|---|---|
| 3,616,454 | A | 10/1971 | Levy et al. |
| 3,980,546 | A | 9/1976 | Caccavo |
| 4,175,662 | A | 11/1979 | Zold |
| 4,315,812 | A | 2/1982 | Karlson |
| 4,375,401 | A | 3/1983 | Catsimpoolas |
| 4,545,888 | A | 10/1985 | Walsh |
| 4,608,147 | A | 8/1986 | Clad |
| 4,655,898 | A | 4/1987 | Poulhes et al. |
| 4,695,548 | A | 9/1987 | Cantor et al. |
| 4,707,233 | A | 11/1987 | Margolis |
| 4,708,782 | A | 11/1987 | Andresen et al. |
| 4,834,862 | A | 5/1989 | Breiner et al. |
| 4,835,263 | A | 5/1989 | Nguyen et al. |
| 4,900,677 | A | 2/1990 | Hewitt |
| 4,948,481 | A | 8/1990 | Mullner |
| 5,062,942 | A | 11/1991 | Kambara et al. |
| 5,169,511 | A | 12/1992 | Allington et al. |
| 5,217,591 | A | 6/1993 | Gombocz et al. |
| 5,242,568 | A | 9/1993 | Her |
| 5,304,487 | A | 4/1994 | Wilding et al. |
| 5,384,022 | A | 1/1995 | Rajasekaran |
| 5,433,837 | A | 7/1995 | Brunk et al. |
| 5,443,704 | A | 8/1995 | Kirkpatrick et al. |
| 5,457,050 | A | 10/1995 | Mazurek |
| 5,538,614 | A | 7/1996 | Han |
| 5,707,812 | A | 1/1998 | Horn et al. |
| 5,717,602 | A | 2/1998 | Kenning |
| 5,800,690 | A | 9/1998 | Chow et al. |
| 5,801,115 | A | 9/1998 | Albers et al. |
| 5,804,684 | A | 9/1998 | Su |
| 5,804,864 | A | 9/1998 | Akiyama |
| 5,827,418 | A | 10/1998 | Haven et al. |
| 5,840,169 | A | 11/1998 | Andersen |
| 5,929,208 | A | 7/1999 | Heller et al. |
| 6,290,831 | B1 | 9/2001 | Liran et al. |
| 6,306,348 | B1 | 10/2001 | Havens et al. |
| 6,319,472 | B1 | 11/2001 | Ackley et al. |
| 6,344,325 | B1 | 2/2002 | Quake et al. |
| 6,365,024 | B1 | 4/2002 | Parce |
| 6,369,893 | B1 | 4/2002 | Christel et al. |
| 6,388,746 | B1 | 5/2002 | Eriksson et al. |
| 6,430,512 | B1 | 8/2002 | Gallagher |
| 6,611,768 | B2 | 8/2003 | Gallagher |
| 6,808,609 | B1 | 10/2004 | Soane et al. |
| 6,834,240 | B2 | 12/2004 | Gallagher |
| 6,867,851 | B2 | 3/2005 | Blumenfeld et al. |
| 6,887,668 | B2 | 5/2005 | Liu et al. |
| 6,919,571 | B2 | 7/2005 | Lai et al. |
| 6,964,736 | B2 | 11/2005 | Quake et al. |
| 7,056,746 | B2 | 6/2006 | Seul et al. |
| 7,108,775 | B2 | 9/2006 | Bahatt et al. |
| 7,122,104 | B2 | 10/2006 | Cabilly et al. |
| 7,150,812 | B2 | 12/2006 | Huang et al. |
| 7,198,703 | B2 | 4/2007 | Rooney et al. |
| 7,413,642 | B2 | 8/2008 | Hassard et al. |
| 7,419,784 | B2 | 9/2008 | Dubrow et al. |
| 7,735,652 | B2 | 6/2010 | Inglis et al. |
| 7,988,840 | B2 | 8/2011 | Huang et al. |
| 8,361,298 | B2 | 1/2013 | Sabin |
| 8,361,299 | B2 | 1/2013 | Sabin |
| 9,012,373 | B2 | 4/2015 | Boles et al. |
| 9,599,590 | B2 | 3/2017 | Sabin et al. |
| 9,719,961 | B2 | 8/2017 | Sabin et al. |
| 10,131,901 | B2 | 11/2018 | Abrams et al. |
| 10,473,619 | B2 | 11/2019 | Sabin et al. |
| 2001/0000103 | A1 | 4/2001 | Rhodes et al. |
| 2002/0076825 | A1 | 6/2002 | Cheng et al. |
| 2002/0170831 | A1 | 11/2002 | Roeth et al. |
| 2002/0187503 | A1 | 12/2002 | Harrold et al. |
| 2003/0151735 | A1 | 8/2003 | Blumenfeld et al. |
| 2003/0170609 | A1 | 9/2003 | Rigler |
| 2003/0190634 | A1 | 10/2003 | Barany et al. |
| 2004/0011650 | A1 | 1/2004 | Zenhausern et al. |
| 2004/0089546 | A1 | 5/2004 | Bahatt et al. |
| 2004/0144651 | A1 | 7/2004 | Huang et al. |
| 2005/0205427 | A1 | 9/2005 | Boschetti et al. |
| 2006/0193752 | A1 | 8/2006 | Levine |
| 2006/0223178 | A1 | 10/2006 | Barber et al. |
| 2007/0284250 | A1 | 12/2007 | Magnant et al. |
| 2007/0286773 | A1 | 12/2007 | Schlautmann et al. |
| 2008/0023399 | A1 | 1/2008 | Inglis et al. |
| 2008/0057557 | A1 | 3/2008 | Margalit |
| 2008/0138809 | A1 | 6/2008 | Kapur et al. |
| 2009/0241216 | A1 | 9/2009 | Wang-Pruski et al. |
| 2009/0308749 | A1 | 12/2009 | Park |
| 2010/0048412 | A1 | 2/2010 | Liu et al. |
| 2010/0059414 | A1 | 3/2010 | Sturm et al. |
| 2010/0126862 | A1 | 5/2010 | Sabin et al. |
| 2010/0233693 | A1 | 9/2010 | Kopf-Sill et al. |
| 2011/0062024 | A1 | 3/2011 | Sabin et al. |
| 2011/0114487 | A1 | 5/2011 | Schmidt et al. |
| 2011/0287436 | A1 | 11/2011 | Shannon et al. |
| 2012/0195809 | A1 | 8/2012 | Wart et al. |
| 2013/0020199 | A1 | 1/2013 | Margalit |
| 2013/0079251 | A1 | 3/2013 | Boles et al. |
| 2013/0217022 | A1 | 8/2013 | Cao et al. |
| 2013/0233714 | A1 | 9/2013 | Sabin et al. |
| 2013/0240360 | A1 | 9/2013 | Sabin et al. |
| 2014/0271602 | A1 | 9/2014 | Zhang et al. |
| 2014/0284213 | A1 | 9/2014 | Sabin et al. |
| 2015/0027891 | A1 | 1/2015 | Puleo et al. |
| 2015/0101932 | A1 | 4/2015 | Sabin et al. |
| 2015/0166986 | A1 | 6/2015 | Boles et al. |
| 2016/0115536 | A1 | 4/2016 | Mead et al. |
| 2016/0370318 | A1 | 12/2016 | Sabin et al. |
| 2017/0239658 | A1 | 8/2017 | Abrams et al. |
| 2017/0240882 | A1 | 8/2017 | Abrams et al. |
| 2017/0254774 | A1 | 9/2017 | Sabin et al. |
| 2020/0041449 | A1 | 2/2020 | Abrams et al. |
| 2021/0062180 | A1 | 3/2021 | Abrams et al. |

FOREIGN PATENT DOCUMENTS

| | | |
|---|---|---|
| CN | 102268426 A | 12/2011 |
| CN | 102305823 A | 1/2012 |
| CN | 103122381 A | 5/2013 |
| CN | 104968784 A | 10/2015 |
| CN | 105408497 A | 3/2016 |
| DE | 102004025650 A1 | 6/2006 |
| EP | 0334615 A2 | 9/1989 |
| EP | 0382426 A2 | 8/1990 |
| EP | 1384067 B1 | 1/2004 |
| GB | 2148325 A | 5/1985 |
| GB | 2148326 A | 5/1985 |
| JP | S62239047 A | 10/1987 |
| JP | S6322254 B2 | 5/1988 |
| JP | H07198680 A | 8/1995 |
| JP | 2000/224980 A | 8/2000 |
| JP | 2002/518672 A | 6/2002 |
| JP | 2002/310992 A | 10/2002 |
| JP | 2002/323477 A | 11/2002 |
| JP | 2004/150170 A | 4/2004 |
| JP | 2005/147957 A | 6/2005 |
| JP | 2005/532545 A | 10/2005 |
| WO | WO 1986/006743 A1 | 11/1986 |
| WO | WO 1996/004000 A1 | 2/1996 |
| WO | WO 1996/023213 A1 | 8/1996 |
| WO | WO 1998/010277 A1 | 3/1998 |
| WO | WO 2002/028516 A1 | 4/2002 |
| WO | WO 2002/044706 A1 | 6/2002 |
| WO | WO 2003/087370 A1 | 10/2003 |
| WO | WO 2005/093388 A1 | 10/2005 |

(56) References Cited

FOREIGN PATENT DOCUMENTS

| | | |
|---|---|---|
| WO | WO 2006/031385 A2 | 3/2006 |
| WO | WO 2006/108101 A2 | 10/2006 |
| WO | WO 2008/016414 A2 | 2/2008 |
| WO | WO 2008/041718 A1 | 4/2008 |
| WO | WO 2010/042766 A1 | 4/2010 |
| WO | WO 2010/048605 A1 | 4/2010 |
| WO | WO 2012/171329 A1 | 12/2012 |
| WO | WO 2013/020089 A2 | 2/2013 |
| WO | WO 2014/059188 A1 | 4/2014 |
| WO | WO 2014/065596 A1 | 5/2014 |
| WO | WO 2014/186819 A1 | 11/2014 |
| WO | WO 2015/040075 A1 | 3/2015 |
| WO | WO 2016/061416 A1 | 4/2016 |
| WO | WO 2016/061556 A1 | 4/2016 |
| WO | WO 2017/040813 A2 | 3/2017 |
| WO | WO 2017/087979 A1 | 5/2017 |
| WO | WO 2017/139669 A1 | 8/2017 |
| WO | WO 2018/067736 A1 | 4/2018 |
| WO | WO 2018/187779 A1 | 10/2018 |
| WO | WO 2019/136301 A1 | 7/2019 |

OTHER PUBLICATIONS

Extended European Search Report for European Application No. 16867354.9 dated Mar. 22, 2019, 9 pages.
International Preliminary Report on Patentability, dated Apr. 9, 2019, for International Application No. PCT/US2017/055193.
International Preliminary Reporton Patentability, dated Aug. 14, 2018, for International Application No. PCT/US2017/017508.
International Preliminary Reporton Patentability, dated May 22, 2018, for International Application No. PCT/US2016/063190.
International Preliminary Reporton Patentability, dated Oct. 8, 2019, for International Application No. PCT/US2018/026603, 8 pages.
International Search Report and Written Opinion, dated Aug. 1, 2018, for International Application No. PCT/US2018/026603.
International Search Report and Written Opinion, dated Mar. 7, 2019, for International Application No. PCT/US2019/012416, 14 pages.
Invitation to Pay Additional Fees, dated Apr. 3, 2017, for International Application No. PCT/US2017/017508.
Lee and Krell, "Generation and analysis of defective genomes of Autographa californica nuclear polyhedrosis virus." Journal of Virology (Jul. 1992); 66(7): 4339-4347.
Tang, et al., "Compression and self-entanglement of single DNA molecules under uniform electric field." PNAS (Sep. 27, 2011); 108 (39): 16153-16158.
Extended European Search Report for European Application No. 17859138.4, dated Apr. 15, 2020, 6 pages.
International Preliminary Report on Patentability, dated Jul. 7, 2020 for International Application No. PCT/US2019/012416, 7 pages.
Wang, Xiaoqing, et al., "Study of Preparation and Restriction Endonuclease of B. cepacia HMW DNA", Biotechnology Bulletin (Dec. 31, 2009); Issue 3, pp. 137-142 (with English Abstract).
Zhang, Ying-xin, et al., "Isolation of the HMW-DNA from Crofton Weed (Ageratina adenophora)", Acta Bot. Boreal. -Occident. Sin. (Dec. 31, 2011); 31(12): 2551-2557 (with English Abstract).
"ABI PRISM 377: DNA Sequencer." Perkin Elmer User's Manual, Part No. 903433, Rev. A. (1995):4-58-5-17.
Adey, et al., "In vitro, long-range sequence information for de novo genome assembly via transposase contiguity." Genome Research (2014); 24 (12): 2041-2049.
Amini, et al., "Haplotype-resolved whole genome sequencing by contiguity preserving transposition and combinatorial indexing." Nature Genetics (2014); 46 (12): 1343-1349.
Ansorge et al., "A simple field gradient technique which leads to sharpening of bands of DNA and to an increase in the number of receivable bases per gel", J. of Biochem. Biophys. Meth., 10:237-243 (1984).
Antunes, et al., "Targeted DNA excision in Arabidopsis by a re-engineered homing endonuclease." BMC Biotechnology (2012); 12: 86.
Australian Patent Examination Report No. 1 corresponding to Australian Application No. 2013329110, dated Jul. 28, 2016.
Bakajin, et al., "Separation of 100-kilobase DNA molecules in 10 seconds." Anal. Chem. (2001); 73 (24): 6053-6056.
Bibin, et al., "Depletion effects in binary hard-sphere fluids." J. Phys.: Condens. Matter, (1996); 8 (50): 10799-10821.
Bogdanove and Voytas, "TAL effectors: customizable proteins for DNA targeting." Science (2011); 333 (6051): 1843-1846.
Boncinelli et al., "An agarose gel resolving a wide range of DNA fragment lengths", Anal. Biochem., 134:40-43 (1983).
Boom et al. "Rapid and Simple Method for Purification of Nucleic Acids." J. Clin. Microbiol. 28.3(1990): 495-503.
Borgström, et al., "Large scale library generation for high throughput sequencing." PLoS One (2011); 6 (4):e19119.
Chan et al., "DNA kinetics in microfabricated devices", Micro Electro Mechanical Systems, 60-63 (2002).
Chang et al., "New Mass-Spectrometry-Compatible Degradable Surfactant for Tissue Proteomics." J. Proteome Res. (2015); 14 (3): 1587-1599.
Chen et al., "An inexpensive microslab gel DNA electrophoresis system with real-time fluorescence detection", Electrophoresis, 27(2):387-393 (2006).
Cheng et al. "Interaction between DNA and Trimethyl-Ammonium Bromides with Different Alkyl Chain Lengths." Scientific World Journal Jan. 16, 2014, vol. 2014, No. 863409, pp. 1-9.
Chiu et al. "Differential Dependence on Chromatin Structure for Copper and Iron Ion Induction of DNA Double-Strand Breaks." Biochem. 34(1995):2653-2661.
Ciulla et al. "A Simple Method for DNA Purification from Peripheral Blood." Anal. Biochem. 174(1988):485-488.
Cong, et al., "Multiplex genome engineering using CRISPR/Cas systems." Science (2013); 339 (6121): 819-823.
Cost, et al., "Directed assembly of DNA molecules via simultaneous ligation and digestion." BioTechniques (2007); 42(1): 84-89.
Costa et al., "Isolation of proteins and nucleic acids by electrophoresis on disposable gel columns", Electrophoresis, 17(4):781-783 (1995).
Cunha, et al., "Polymer-Mediated Compaction and Internal Dynamics of Isolated *Escherichia coli* Nucleoids." J. Struct. Biol. (2001); 136 (1): 53-66.
Davis, et al., "Deterministic hydrodynamics: taking blood apart." Proc. Natl. Acad. Sci. U.S.A. (2006); 103 (40): 14779-14784.
Diehl et al. "BEAMing: Single-Molecule PCR on Microparticles in Water-in-Oil Emulsions." Nat. Methods. 3.7(2006):551-559.
DNA Analysis, The Development of a Portable High-Speed DNA Analysis Device—Paving the Way Towards Point-Of-Care Diagnosis and Advanced Medical Treatment, http://www.azonano.com/Details.asp2Article ID=1783 (2006).
Duke, "Monte carlo reptation model of gel electrophoresis: steady state behavior." J. Chem. Phys. (1990); 93 (12): 9049-9054.
Duyster, et al., "Translocations involving anaplastic lymphoma kinase (ALK)" Oncogene (2001); 20 (40): 5623-5637.
Eckhardt, "A rapid method for the identification of plasmid desoxyribonucleic acid in bacteria." Plasmid (1978); 1(4): 584-588.
Esvelt et al., "Genome-scale engineering for systems and synthetic biology" Mol Syst Biol. (2013);9:641.
Extended European Search Report for European Application No. 15851562.7 dated Jan. 29, 2018, 6 pages.
Full English language translation of Quan Du WO 2012/171329 A1, patent published Jun. 12, 2012, 54 pages.
Gardella, et al., "Detection of circular and linear herpesvirus DNA molecules in mammalian cells by gel electrophoresis." J. Virol. (1984); 50 (1): 248-254.
Gasiunas, et al., "Cas9-crRNA ribonucleoprotein complex mediates specific DNA cleavage for adaptive immunity in bacteria." ProcNatl Acad Sci U.S.A. (2012); 109 (39): E2579-2586.
Girvitz et al. "A rapid and efficient procedure for the purification of DNA from agarose gels", Analytical Biochemistry, 106(2):492-496 (1980).

(56) References Cited

OTHER PUBLICATIONS

Gnirke et al., "Solution hybrid selection with ultra-long oligonucleotides for massively parallel targeted sequencing." Nat Biotechnol. (2009); 27 (2): 182-189.
Goryshin et al. "Tn5 in vitro Transposition." J. Biol. Chem. 273. 13(1998):7367-7374.
Green et al. "Charting a Course for Genomic Medicine from Base Pairs to Bedside." Nature. 470(2011):204-213.
Griffin, IV, et al. "In vitro Transposition of Tn552: A Tool for DNA Sequencing and Mutagenesis." Nucleic Acids Res. 27.19(1999):3859-3865.
Hamzah, "The effect of viscoelastic fluids on flows generated by spherical objects during sedimentation." PhD thesis, Massachusetts Institute of Technology, 2012, 27 pages.
Hanemaaijer et al. "Characterization of Clean and Fouled Ultrafiltration Membranes." Desalination, 68(1988): 93-108.
Heller et al., "Microelectrophoresis for the separation of DNA fragments", Electrophoresis, 13(1):512-520 (1992).
Hoffman, et al., "Hydrogels for biomedical applications." Advanced Drug Discovery Reviews (2002); 54: 3-12.
Hogan and Austin, "Importance of DNA stiffness in protein-DNA binding specificity." Nature (1987); 329 (6136): 263-266.
Holland, et al., "Isolation and characterization of a small catalytic domain released from the adenylate cyclase from *Escherichia coli* by digestion with trypsin." The Journal of Biological Chemistry (1988); 263 (29): 14661-14668.
Hsu et al., "Development and applications of CRISPR-Cas9 for genome engineering." Cell (2014); 157 (6): 1262-1278.
Hsu, et al., "DNA targeting specificity of RNA-guided Cas9 nucleases." Nat Biotechnol. (2013); 31 (9): 827-832.
Huang, et al., "Continuous Particle Separation Through Deterministic Lateral Displacement." Science (2004); 304: 987-990.
Huang, et al., "A DNA prism for high-speed continuous fractionation of large DNA molecules." Nat. Biotechnol. (2002); 20 (10): 1048-1051.
Hughes, et al., "Expression profiling using microarrays fabricated by an ink-jet oligonucleotide synthesizer." Nat Biotechnol. (2001); 19(4): 342-347.
Inglis, et al., "Critical particle size for fractionation by deterministic lateral displacement." Lab Chip (2006); 6 (5): 655-658.
Inglis, et al., "Determining blood cell size using microfluidic hydrodynamics." J. Immunol. Methods (2008); 329 (1): 151-156.
Inoue et al., "I-shaped microchannel array chip for parallel electrophoretic analyses", Analytical Chemistry, 79:2168-2173 (2007).
International Preliminary Report on Patentability for International Application No. PCT/US2012/049603, dated Feb. 4, 2014.
International Preliminary Report on Patentability for International Application No. PCT/US2013/064403, dated Apr. 14, 2015.
International Preliminary Report on Patentability for International Application No. PCT/US2015/055833, dated Apr. 18, 2017.
International Preliminary Report on Patentability for International Application No. PCT/US2009/060065, dated Dec. 7, 2010.
International Preliminary Report on Patentability, dated Apr. 18, 2017, for International Application No. PCT/US2015/056104, 8 pages.
International Search Report and the Written Opinion for International Application No. PCT/US2013/064403, dated Jan. 24, 2014.
International Search Report and Written Opinion for International Application No. PCT/US2012/049603, dated May 17, 2013.
International Search Report and Written Opinion for International Application No. PCT/US2015/055833, dated Feb. 2, 2016.
International Search Report and Written Opinion, dated Dec. 11, 2017, for International Application No. PCT/US2017/055193.
International Search Report and Written Opinion, dated Feb. 8, 2010, for International Application No. PCT/US2009/060065.
International Search Report and Written Opinion, dated Feb. 12, 2016, for International Application No. PCT/US2015/056104.
International Search Report and Written Opinion, dated Feb. 3, 2017, for International Application No. PCT/US2016/063190.
International Search Report and Written Opinion, dated Jun. 27, 2017, for International Application No. PCT/US2017/017508.
Japanese Office Action dated Jun. 14, 2016 and corresponding to Japanese Application No. 2014-524127 (and English translation), 7 pages.
Jinek, et al., "A programmable dual-RNA-guided DNA endonuclease in adaptive bacterial immunity." Science (2012); 337 (6096): 816-821.
Johnson et al., "Sizing of DNA fragments by flow cytometry", Proc. SPIE, 1895:69-78 (1993).
Kaabouch et al., "An analysis system for DNA gel electrophoresis images based on automatic thresholding and enhancement", Electro/Information Technology, 2007 IEEE International Conference on May 17-20, 2007, pp. 26-31.
Karvelis, et al., "Programmable DNA cleavage in vitro by Cas9." Biochem Soc Trans. (2013); 41 (6): 1401-1406.
Khandurina et al., "Micropreparative Fraction Collection in Microfluidic Devices", Anal. Chem., 74(7):1737-1740 (2002).
Kumar et al., "Pyrrolidine Nucleic Acids: DNA/PNA Oligomers with 2-Hydroxy/Aminomethyl-4(thymin-1-yl)pyrrolidine-N-acetic acid", Organic Letters, 3(9):1269-1272 (2001).
Kunkel et al. "Analysis of Human Y-Chromosome-Specific Reiterated DNA in Chromosome Variants." PNAS. 74.3(1977):1245-1249.
La Spada and Taylor, "Repeat expansion disease: progress and puzzles in disease pathogenesis." Nature Reviews Genetics (2010); 11: 247-258.
Laemmli, "Cleavage of structural proteins during the assembly of the head of bacteriophage T4." Nature (1970); 227: 680-685.
Lagriffoul et al., "The Synthesis, Co-Oligomerization and Hybridization of a Thymine-Thymine Heterodimer Containing PNA", Bioorganic and Medical Chemistry Letters, 4:1081-1082 (1994).
Lam et al., "Genome mapping on nanochamlel arrays for structural variation analysis and sequence assembly." Nat. Biotechnol. (2012); 30 (8): 771-776.
Ledford, Heidi, "AstraZeneca launches project to sequence 2 million genomes." Nature: International Weekly Journal of Science (2016); 532 (7600): 427.
Lerman, et al., "A transition to a compact form of DNA in polymer solutions." Proc. Nat. Acad. Sci. U.S.A. (1971); 68 (8):1886-1890.
Li et al., "A Simultaneous Space Sampling Method for DNA Fraction Collection Using a Comb Structure in Microfluidic Devices." Electrophoresis (2011); 32(23): 3392-3398.
Li et al., "On-chip fraction collection for multiple selected ssDNA fragments using isolated extraction channels." Journal of Chromatography A (2011); 1218(7): 997-1003.
Li et al., "Design of a PMMA Chip for Selective Extraction of Size-Fractioned DNA", Proceedings of the 1st IEEE International Conference on Nano/Micro Engineered and Molecular Systems, Zhuhai China, Jan. 18-21, 2006, pp. 105-109.
Li et al., "Design, simulation and optimization of a miniaturized device for size-fractioned DNA extraction", Electrophoresis (2007); 28(24):4661-4667.
Lin et al., "Addressable electric fields for size-fractioned sample extraction in microfluidic devices", Anal. Chem.,77(14):4338-4347 (2005).
Lin et al., "Selective extraction of size-fractioned DNA samples in microfabricated electrophoresis devices", Journal of Chromatography, 1010(2):255-268 (2003).
Liu et al., "DNA fragment analysis by an affordable multiple-channel capillary electrophoresis system", Electrophoresis, 24(1-2):93-95 (2003).
Liu et al., "pK-Matched Running Buffers for Gel Electrophoresis." Analytical Biochemistry (1999); 270(1): 112-122.
Loutherback, et al., "Deterministic microfluidic ratchet." Phys. Rev. Lett. (2009); 102 (4): 045301.
Loutherback, et al., "Deterministic separation of cancer cells from blood at 10 ml/min." AIP advances (2012); 2 (042107).
Loutherback, et al., "Improved performance of deterministic lateral displacement arrays with triangular posts." Microfluid. Nanofluid. (2010); 9 (6): 1143-1149.

(56) References Cited

OTHER PUBLICATIONS

Lundqvist et al., "Electrophoretic separation and confocal laser-induced fluorescence detection at ultralow concentrations in constricted fused-silica capillaries", Electrophoresis, 24(11):1737-1744 (2003).
Mali, et al., "RNA-guided human genome engineering via Cas9." Science (2013); 339 (6121): 823-826.
Margulies et al. "Genome Sequencing in Microfabricated High-Density Picolitre Reactors." Nature. 437.7057(2005):376-380.
Marshall et al., "Analytical micro-preparative electrophoresis: Quantitation of phosphoglucose isomerase isoenzymes", Anal. Biochem., 91(1):283-292 (1978).
Maydan, et al., "Electrophoretic High Molecular Weight DNA Purification Enables Optical Mapping." Boreal Genomics (2013); 1 page.
Meyer, et al., "Expanding Proteome Coverage with Orthogonal-specificity α-Lytic Proteases." Molecular & Cellular Proteomics (2014); 13 (3): 823-835.
Minalla et al., "Automated DNA fraction collection on glass microchips", Micro Total Analysis Systems, 2:946-948 (2002).
Morris, et al., "Fusion of a kinase gene, ALK, to a nucleolar protein gene, NPM, in non-Hodgkin's lymphoma." Science (1994); 263 (5151): 1281-1284.
Morton et al. "Crossing Microfluidic Streamlines to Lyse, Label and Wash Cells." Lab on a Chip. 8.9(2008): 1448-1453.
New England_Restriction_Buffer, NEBuffer Performance Chart with Restriction Enzymes. 2013 [online], [Retrieved on May 23, 2017], Retrieved from the Internet: <URL: https://www.neb.eom/-/media/NebUs/Files/nebuffer-performance-chart-with-restrictionenzymes.pdf>.
Nolin, et al., "Expansion of the Fragile X CGG Repeat in Females with Premutation or Intermediate Alleles." Am. J. Hum. Genet. (2003); 72 (2): 454-464.
Noolandi, and Chantal, In Methods in Molecular Biology vol. 12: Pulsed-field gel electrophoresis. Ed. Burmeister, Afargit, and Ulanovsky, Levy. Humana., pp. 73-103 and 135-143 (1992).
Olsen, et al., "Trypsin Cleaves Exclusively C-terminal to Arginine and Lysine Residues." Molecular & Cellular Proteomics (2004); 3: 608-614.
Olson, et al., "The structure of isometric capsids of bacteriophage t4." Virology (2001); 279 (2): 385-391.
Pamme, "Continuous flow separations in microfluidic devices." Lab Chip (2007); 7 (12): 1644-1659.
Pelletier, et al., "Physical manipulation of the escherichia coli chromosome reveals its soft nature." Proc. Natl. Acad. Sci. U.S.A. (2012); 109 (40): E2649-E2656.
Persat et al., "Purification of Nucleic Acids from Whole Blood Using Isotachophoresis." Anal. Chem. (2009); 81 (22): 9507-9511.
Peterson et al., "Synthesis and oligomerization of Nα-Boc-Nα-(thymin-1-ylacetyl)ornithine", Bioorganic and Medical Chemistry Letters, 6:793-796 (1996).
Petty et al., "Characterization of DNA size determination of small fragments by flow cytometry", Anal. Chem., 67:1755 (1995).
Pluen, t al., "Diffusion of Macromolecules in Agarose Gels: Comparison of Linear and Globular Configurations." Biophysical Journal (1999); 77 (1): 542-552.
Rampino et al., "Apparatus for gel electrophoresis with continuous monitoring of individual DNA molecules by video epifluorescence microscopy", Anal. Biochem., 194(2):278-283 (1991).
Ren, et al., "A Simplified Method to Prepare PCR Template DNA for Screening of Transgenic and Knockout Mice." Journal of Biological Chemistry (2015); 290 45): 27248-27260.
Riehn et al. "Restriction Mapping in Nanofluidic Devices." PNAS. 102(2005):10012-10016.
Rittié and Perbal, "Enzymes used in molecular biology: a useful guide." Journal of Cell Communication and Signaling (2008); 2(1-2): 25-45.
Robertson et al. "Diffusion of Isolated DNA Molecules: Dependence on Length and Topology." PNAS. 103.19(2006):7310-7314.
Rothberg et al. "An Integrated Semiconductor Device Enabling Non-Optical Genome Sequencing." Nature 475.7356(2011):348-352.
Scharenberg, et al., "Genome engineering with TAL-effector nucleases and alternative modular nuclease technologies." Curr Gene Ther. (2013); 13 (4): 291-303.
Schoch, et al., "Rapid and selective extraction, isolation, preconcentration, and quantitation of small RNAs from cell lysate using on-chip isotachophoresis." Lab on a Chip (2009); 9: 2145-2152.
Shalem et al., "Genome-scale CRISPR-Cas9 knockout screening in human cells." Science (2014); 343 (6166): 84-87.
SIGMA_P8340, Protease Inhibitor Cocktail for use with mammalian cell and tissue extracts. Catalog No. P8340. Sigma-Aldrich. 2010 [online], [Retrieved on Mar. 20, 2017], Retrieved from the Internet: <URL: https://www.sigmaaldrich.eom/content/dam/sigmaaldrich/docs/Sigma/Datasheet/5/p8340dat.pdf>.
Singh-Gasson, et al., "Maskless fabrication of light-directed oligonucleotide microarrays using a digital micromirror array." Nat Biotechnol. (1999); 17 (10): 974-978.
Smith et al. "A Physical Map of the *Escherichia coli*K 12 Genome." Science. 236.4807(1987):1448-1453.
Stoddard, et al., "Homing endonucleases: from microbial genetic invaders to reagents for targeted DNA modification." Structure (2011); 19 (1): 7-15.
Suh, E.R., et al., "Semi-automated quantification of C9orf72 expansion size reveals inverse correlation between hexanucleotide repeat No. and disease duration in frontotemporal degeneration." Acta Neuropathol (2015); 130(3): 363-372.
Sun et al., "Electrophoretic chip for high-fidelity fractionation of double-stranded DNA", Electrophoresis, 28(10):1572-1578 (2007).
Sutherland et al., "Electronic imaging system for direct and rapid quantitation of fluorescence from electrophoretic gels: application to ethidium bromide-stained DNA", Anal. Biochem., 163(2):446-457 (1987).
Tabak et al., "A method for the recovery of DNA from agarose gels", Nucleic Acids Research, 5(7): 2321-2332 (1978).
Tan, et al., "Gel Electrophoresis: DNA Science without the DNA!," Biochemistry and Molecular Biology Education (2007); 35 (5): 342-349.
Tarn, et al., "On-chip processing of particles and cells via multilaminar flow streams." Anal. Bioanal. Chem. (2014); 406: 139-161.
Tegenfeldt, et al., "The dynamics of genomic-length DNA molecules in 100-nm channels." Proc. Natl. Acad. Sci. U.S.A. (2004); 101 (30): 10979-10983.
Tomkinson, et al., "Location of the active site for enzyme-adenylate formation in DNA ligases." PNAS (1991); 88 (2): 400-404.
Urnov, et al., "Genome editing with engineered zinc finger nucleases." Nat Rev Genet. (2010); 11 (9): 636-646.
Volkmuth and Austin, "DNA electrophoresis in microlithographic arrays." Nature (1992); 358 (6387): 600-602.
Wang et al. "PacBio-LITS: a large-insert targeted sequencing method for characterization of human disease-associated chromosomal structural variations." BMC Genomics (2015); 16: 214.
Wang et al., "A simple microfluidic system for efficient capillary electrophoretic separation and sensitive fluorimetric detection of DNA fragments using light-emitting diode and liquid-core waveguide techniques", Electrophoresis (2005); 26(19):3602-3608.
Wang, et al., "Genetic screens in human cells using the CRISPR-Cas9 system." Science (2014); 343(6166): 80-84.
Wang, et al., "IRDL Cloning: A One-Tube, Zero-Background, Easy-to-Use, Directional Cloning Method Improves Throughput in Recombinant DNA Preparation." PLoS One (2014); 9(9): e107907.
Wang, et al., "Stretching DNA with optical tweezers." Biophys. J. (1997); 72 (3): 1335-1346.
Wilson, et al., "Engineered DNA ligases with improved activities in vitro." Protein Engineering, Design & Selection (2013); 26 (7): 471-478.
Worcel et al. "On the Structure of the Folded Chromosome of *Escherichia coli*." J. Mol. Biol. 71.2(1972):127-147.
Xiao et al., "CE with LED-based detection: An update", Electrophoresis, 30(1):189-202 (2008).

(56) References Cited

OTHER PUBLICATIONS

Zakharov et al., "Recovery of SDS-protein and DNA using commercial automated gel electrophoresis apparatus", Appl. Theor. Electrophor., 5(1):25-29 (1995).

Zalewski et al., "Electrokinetic sorting and collection of fractions for preparative capillary electrophoresis on a chip", Lab on a Chip (2008); 8 (5): 801-809.

Zaret et al. "Micrococcal Nuclease Analysis of Chromatin Structure." Curr. Protoc. Mol. Biol. S69(2005):21.1.1-21.1.17.

Zetsche et al., "Cpf1 is a single RNA-guided endonuclease of a class 2 CRISPR-Cas system." Cell (2015); 163 (3): 759-771.

Zimmerman and Minton, "Macromolecular crowding: biochemical, biophysical, and physiological consequences." Annu. Rev. Biophys. Biomol. Struct. (1993); 22 (1): 27-65.

\* cited by examiner

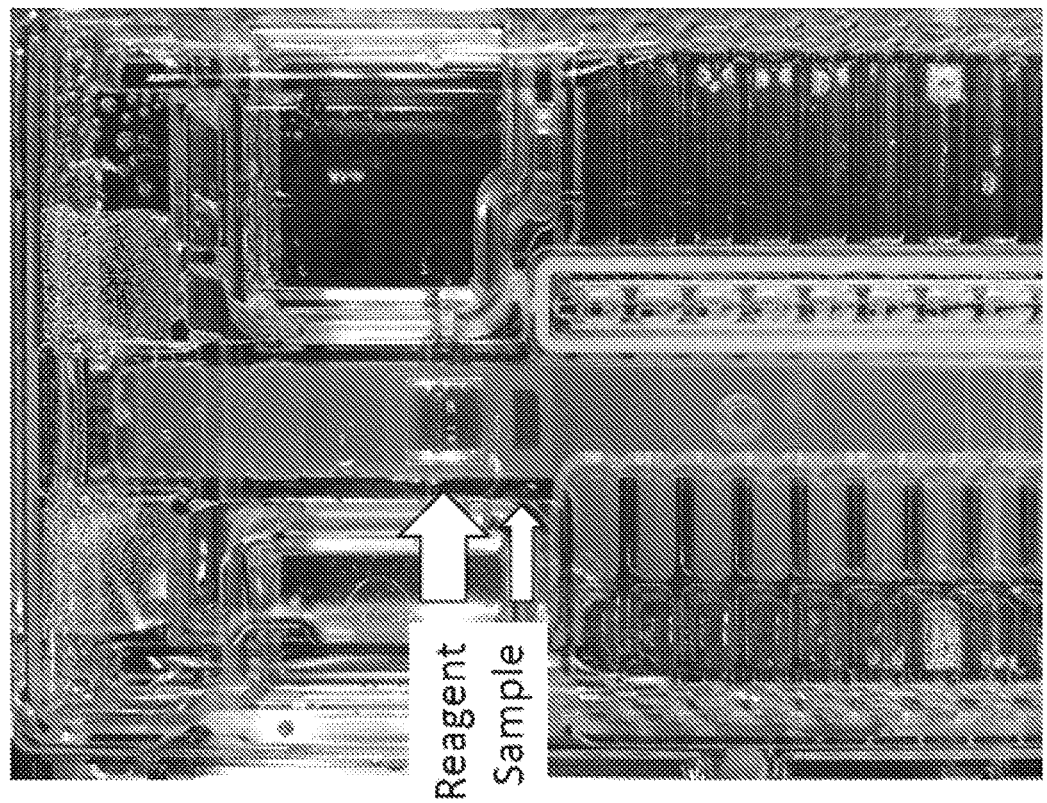
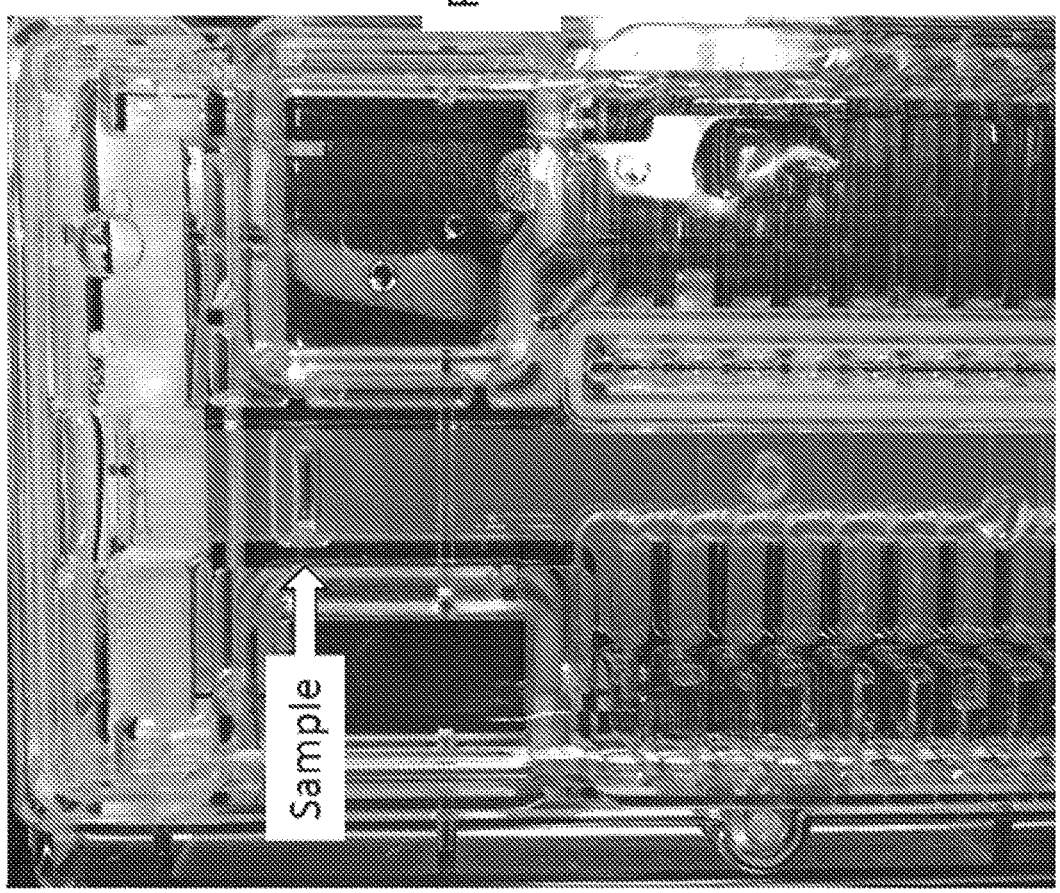
FIGURE 2

SEQUENCE LISTING

```
<160> NUMBER OF SEQ ID NOS: 31

<210> SEQ ID NO 1
<211> LENGTH: 103
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (3)..(22)
<223> OTHER INFORMATION: n is a, c, g, or t
```

```
<400> SEQUENCE: 1
ggnnnnnnnn nnnnnnnnnn nngtttagaa gctagaaata gcaagttaaa ataaggctag     60
tccgttatca acttgaaaaa gtggcaccga gtcggtgctt ttt                      103

<210> SEQ ID NO 2
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 2
gaaaagaaca gttacgtagc                                                 20

<210> SEQ ID NO 3
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 3
ccagaagctt cacaagaccg                                                 20

<210> SEQ ID NO 4
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 4
attccttata ttcaccccca                                                 20

<210> SEQ ID NO 5
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 5
cattccttat attcaccccc                                                 20

<210> SEQ ID NO 6
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 6
tagggaaaag aacagttacg tagc                                            24

<210> SEQ ID NO 7
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 7
aaacgctacg taactgttct tttc                                            24
```

```
<210> SEQ ID NO 8
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 8
taggttgaaa gcagcagaat tctt                                              24

<210> SEQ ID NO 9
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 9
aaacaagaat tctgctgctt tcaa                                              24

<210> SEQ ID NO 10
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 10
taggattcct tatattcacc ccca                                              24

<210> SEQ ID NO 11
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 11
aaactggggg tgaatataag gaat                                              24

<210> SEQ ID NO 12
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 12
taggtctatc aacaaattgc tagg                                              24

<210> SEQ ID NO 13
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 13
aaaccctagc aatttgttga taga                                              24

<210> SEQ ID NO 14
<211> LENGTH: 136
<212> TYPE: DNA
<213> ORGANISM: Artificial Sequence
<220> FEATURE:
<223> OTHER INFORMATION: Synthetic Polynucleotide
<220> FEATURE:
```

<221> NAME/KEY: misc_feature
<222> LOCATION: (36)..(55)
<223> OTHER INFORMATION: n is a, c, g, or t

<400> SEQUENCE: 14
cgctcgcacc gctagctaat acgactcact ataggnnnnn nnnnnnnnnn nnnnngtttt    60
agagctagaa atagcaagtt aaaataaggc tagtccgtta tcaacttgaa aaagtggcac   120
cgagtcggtg cttttt                                                  136

<210> SEQ ID NO 15
<211> LENGTH: 26
<212> TYPE: DNA
<213> ORGANISM: Artificial Sequence
<220> FEATURE:
<223> OTHER INFORMATION: Synthetic Polynucleotide

<400> SEQUENCE: 15
cgctcgcacc gctagctaat acgact                                        26

<210> SEQ ID NO 16
<211> LENGTH: 27
<212> TYPE: DNA
<213> ORGANISM: Artificial Sequence
<220> FEATURE:
<223> OTHER INFORMATION: Synthetic Polynucleotide

<400> SEQUENCE: 16
aaaaagcacc gactcggtgc cactttt                                       27

<210> SEQ ID NO 17
<211> LENGTH: 103
<212> TYPE: DNA
<213> ORGANISM: Artificial Sequence
<220> FEATURE:
<223> OTHER INFORMATION: Synthetic Polynucleotide
<220> FEATURE:
<221> NAME/KEY: misc_feature
<222> LOCATION: (3)..(22)
<223> OTHER INFORMATION: n is a, c, g, or t

<400> SEQUENCE: 17
ggnnnnnnnn nnnnnnnnnn nngttttaga gctagaaata gcaagttaaa ataaggctag    60
tccgttatca acttgaaaaa gtggcaccga gtcggtgctt ttt                     103

<210> SEQ ID NO 18
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 18
caagtcaccc gctttctttc                                               20

<210> SEQ ID NO 19
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 19
gactttggag atgttttctc                                               20

```
<210> SEQ ID NO 20
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 20
gaagaaaaca tggcacaaat                                                   20

<210> SEQ ID NO 21
<211> LENGTH: 20
<212> TYPE: DNA
<213> ORGANISM: Artificial Sequence
<220> FEATURE:
<223> OTHER INFORMATION: Synthetic Polynucleotide

<400> SEQUENCE: 21
caatgggtca gataactcaa                                                   20

<210> SEQ ID NO 22
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 22
taggcaagtc acccgctttc tttc                                              24

<210> SEQ ID NO 23
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 23
aaacgaaaga aagcgggtga cttg                                              24

<210> SEQ ID NO 24
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 24
taggactttg gagatgtttt ctc                                               23

<210> SEQ ID NO 25
<211> LENGTH: 23
<212> TYPE: DNA
<213> ORGANISM: Artificial Sequence
<220> FEATURE:
<223> OTHER INFORMATION: Synthetic Polynucleotide

<400> SEQUENCE: 25
aaacgagaaa acatctccaa agt                                               23

<210> SEQ ID NO 26
<211> LENGTH: 24
<212> TYPE: DNA
<213> ORGANISM: Artificial Sequence
<220> FEATURE:
<223> OTHER INFORMATION: Synthetic Polynucleotide
```

```
<400> SEQUENCE: 26
taggaggggc gcccaatttt gtct                                          24

<210> SEQ ID NO 27
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 27
aaacagacaa aattgggcgc ccct                                          24

<210> SEQ ID NO 28
<211> LENGTH: 27
<212> TYPE: DNA
<213> ORGANISM: Artificial Sequence
<220> FEATURE:
<223> OTHER INFORMATION: Synthetic Polynucleotide

<400> SEQUENCE: 28
taggtctatc aacaaattgc taggagg                                       27

<210> SEQ ID NO 29
<211> LENGTH: 24
<212> TYPE: DNA
<213> ORGANISM: Artificial Sequence
<220> FEATURE:
<223> OTHER INFORMATION: Synthetic Polynucleotide

<400> SEQUENCE: 29
aaaccctagc aatttgttga taga                                          24

<210> SEQ ID NO 30
<211> LENGTH: 20
<212> TYPE: DNA
<213> ORGANISM: Artificial Sequence
<220> FEATURE:
<223> OTHER INFORMATION: PCR primer

<400> SEQUENCE: 30
gttggaacct cttacgtgcc                                               20

<210> SEQ ID NO 31
<211> LENGTH: 18
<212> TYPE: DNA
<213> ORGANISM: Artificial Sequence
<220> FEATURE:
<223> OTHER INFORMATION: PCR primer

<400> SEQUENCE: 31
aaaagcaccg actcggtg                                                 18
```

PREPARATIVE ELECTROPHORETIC METHOD FOR TARGETED PURIFICATION OF GENOMIC DNA FRAGMENTS

CROSS-REFERENCE TO RELATED APPLICATIONS

This application claims priority to International Patent Application No. PCT/US2016/063190, filed Nov. 21, 2016, and entitled "Preparative Electrophoretic Method for Targeted Purification of Genomic DNA Fragments," which in turn claims benefit of and priority to U.S. Provisional Patent Application No. 62/258,384, filed Nov. 20, 2015, and entitled "Preparative Electrophoretic Method for Targeted Purification of Genomic DNA Fragments." The disclosures of each of the above-referenced applications are herein incorporated by reference in their entireties.

DESCRIPTION OF THE TEXT FILE SUBMITTED ELECTRONICALLY

The contents of the text file submitted electronically herewith are incorporated herein by reference in their entirety: a computer readable format copy of the sequence listing (filename: SAGS_011_N01US_SeqList_ST25.txt, date recorded: Oct. 26, 2022, file size 7,171 bytes).

INTRODUCTION

Due to the high cost of whole genome sequencing and the complexity of whole genome sequence analyses, most next-generation sequencing experiments seek to examine targeted regions of the genome, such as all protein coding regions (whole exome sequencing, "WES"), or a specific subset of genes (or a specific subset of genomic regions) in so-called targeted sequencing investigations. When such targeted sequencing experiments are carried out using barcoded sequencing adapters, many such samples can be pooled and run together in a single sequencing run, thereby lowering the per sample sequencing cost dramatically. For this reason, the vast majority of NGS performed today (and for the past several years) is WES or targeted sequencing.

Most popular methods for preparing targeted sequencing libraries fall into two general strategies 1) hybridization capture, or 2) amplicon library construction.

In the hybridization capture approach, targeted genomic DNA fragments are denatured to single-stranded form and hybridized in solution to biotin-tagged single-stranded nucleic acid probes (also known as "baits"). After hybridization, the biotin-tagged hybrids are captured onto avidin or streptavidin-coated micro-particles (usually paramagnetic particles), and are then separated from the solution phase un-targeted genomic DNA by magnetic or centrifugal collection of the particles.

Library construction can precede or follow the targeted sequence capture. In the most popular forms of the technique (e.g., Agilent Sureselect and Illumina Whole Exome kit), DNA fragmentation, end repair, and attachment of sequencing adapters are performed prior to hybridization capture. However, in some targeted sequencing protocols, hybridization capture precedes library construction (Wang et al. BMC Genomics, (2015) 16:214; DOI 10.1186/s12864-015-1370-2).

Hybridization probes can be single stranded DNA, RNA, or analogs thereof. Many find it convenient to design capture probes as DNA oligonucleotides containing a strong RNA polymerase promoter (such as a T7 RNA polymerase promoter) so that biotinylated single-stranded RNA capture probes can be inexpensively produced by in vitro transcription reactions. Such methods are particularly useful when the same targeted panel needs to be examined in a large number of samples (Gnirke et al., Nature Biotechnology, (2009) 27:182).

In the amplicon library method, target regions for sequencing are first amplified by PCR, and then the PCR products are used as the DNA input for NGS library construction. The most popular examples of this method are the AmpliSeq targeted sequencing kits from Life Technologies (for example). Amplicon sequencing methods are popular in clinical laboratories, since PCR allows the use of smaller input sample amounts (1-10 ng input DNA).

Both methods of targeted sequencing have a common disadvantage in that they require a relatively large number of nucleic acid reagents: biotinylated probes in the hybrid capture method, or PCR primer pairs in the case of amplicon sequencing. This is especially a concern when using common short-read sequencing technologies like Illumina or Ion Torrent (typical raw read lengths <400 bp) to examine a long multi-kilobase (kb) region of genomic DNA. A related issue is complexity of designing and optimizing kits that that use such complex sets of probes or primers with the required specificity/stringency in a convenient multiplex format.

Another difficulty with current targeted sequencing methods is the difficulty in applying them to very large DNA molecules (10 kb up to low single megabase pairs (mb)), for study of long range genome structure and rearrangements, and for long-range phasing and haplotyping. For instance, long-range PCR is unreliable for distances greater than 10 kb and most commercially available DNA extraction methods do not reliably produce DNA greater than 50-100 kb.

SUMMARY OF SOME OF THE EMBODIMENTS

In some embodiments of the present disclosure, a method for isolating specific fragments of genomic DNA is provided and comprises:
  providing a sample containing high-molecular-weight (HMW) DNA;
  entrapping the sample in a gel matrix wherein the HMW DNA has extremely low electrophoretic mobility.
  exposing the gel matrix with the entrapped sample to a lysis reagent to release the HMW DNA from other sample contaminants.
  subjecting the gel matrix with the entrapped sample to an electrophoretic field such that sample contaminants and lysis reagents are removed from the gel matrix, leaving behind the gel-entrapped purified HMW DNA;
  subjecting the gel matrix with the entrapped purified DNA to treatment with DNA cleavase reagents configured to cleave at specific DNA sequences within the sample DNA, thereby liberating defined segments of the sample as fragments of reduced size, where the liberated defined DNA fragments have a much greater electrophoretic mobility than the remainder of the uncleaved HMW sample DNA;
  subjecting the gel matrix to an electrophoretic field such that the specifically excised DNA fragments are physically separated from the remainder of the uncleaved HMW sample DNA; and
  isolating the specifically excised and electrophoretically separated DNA fragments from the gel matrix, leaving behind the uncleaved remainder of the HMW DNA sample still entrapped in the gel matrix.

In some embodiments, a similar method is provided which comprises a plurality of the above-noted steps.

In some embodiments, the sample comprises a liquid suspension of intact cells (e.g., animal, plant, bacterial, fungal, archebacterial, protozoan) or intact virus particles.

In some embodiments, the gel matrix comprises an agarose hydrogel at a concentration between about 0.2% and about 5% (weight/volume).

In some embodiments of the invention, the lysis reagent comprises an anionic detergent at a concentration between 0.05% and 10%. In some embodiments of the invention, the anionic detergent is sodium dodecyl sulfate (SDS).

In some embodiments, the size of the DNA liberated by lysis of the sample is >10 megabase pairs in length, and the size of the DNA fragments released by the specific cleavase reagents is <2 megabase pairs in length.

In some embodiments which utilize bacteria, plant, or fungal cells, additional enzymatic reagent treatments are used to remove the cell walls prior to cell lysis.

In some embodiments, the DNA fragments specifically released by the specific cleavase reagents are isolated from the gel matrix by electroelution into an elution module containing liquid buffer.

In some embodiments, methods and apparatuses are provided for entrapment of the sample, and purification of the sample DNA. General methods for enzymatic treatment of the purified entrapped sample DNA are described in co-pending PCT application no. PCT/US2015/055833, the entire disclosure of which is herein incorporated by reference in its entirety.

In some embodiments, the DNA cleavase reagents comprise one or more RNA-guided endonuclease compositions. For example, one such composition is based on the CRISPR/Cas9 system (see below) comprising the Cas9 protein with guide RNAs that enable the guide-RNA-Cas9 complex to cleave at specific user-designated sites in the genomic DNA.

Other sequence-specific DNA cleavase reagents may be used with some embodiments, such as other RNA-guided endonuclease systems, engineered zinc-finger nucleases, engineered transcription activator-like nucleases, and engineered meganucleases (Zetsche et al., (2015) Cell 163:759; Hsu P D, et al., (2014) Cell 157:1262; Esvelt and Wang, (2013) Mol Syst Biol. 9: 641; Stoddard B L, (2011) Structure 19:7; Urnov F D, et al., (2010) Nat Rev Genet. 11:636; Bogdanove and Voytas, (2011) Science 333:1843; Scharenberg A M, et al., (2013) Curr Gene Ther. 13(4):291).

The Cas9 protein is major component of the clustered regularly interspaced short palindromic repeat (CRISPR) system that is an adaptive immune system in bacteria that degrades DNA sequences of invading viruses (Gasiunas, G., et al., (2012) Proc Natl Acad Sci USA, 109:E2579; Jinek, M., et al., Science, (2012) 337: 816). Cas9 is a DNA endonuclease with a unique mechanism for achieving its binding specificity. Cas9 complexes with CRISPR RNAs that direct the protein to bind and cleave DNA sequences that are complementary to these RNA sequences. In the endogenous CRISPR system, multiple RNAs cooperate to direct Cas9, but recently, Cas9 binding to a specific DNA sequence directed by a single chimeric gRNA has been demonstrated. Henceforth, we refer to chimeric gRNAs as simply gRNAs, unless otherwise specified. The discovery of Cas9 has catalyzed great interest in using this protein for genome editing as designing a targeted endonuclease now becomes as simple as ordering an oligonucleotide (Cong, L., et al., Science, (2013) 339:819; Mali, P., et al., (2013) Science 339:823). DNA cleavage by Cas9 is typically performed in vivo by expressing both the Cas9 protein and guide RNA in a cell. However, in vitro DNA cleavage can also be achieved by combining purified Cas9 protein with gRNA and adding DNA template (Karvelis et al., (2013) Biochem Soc Trans 41:1401, PMID 24256227). In effect, the guide-RNA-Cas9 complex serves as a user-customizable restriction enzyme, allowing cleavage at or near virtually any known DNA sequence. In this way, users can configure combinations of CRISPR/Cas9 reagents to cleave in the regions surrounding specific DNA regions of interest in the sample DNA.

The most commonly used Cas9 nuclease comes from the *Streptococcus pyogenes* bacteria (SpCas9), and it specifically Cleaves DNA with efficiencies approaching 100% both in vitro and in vivo (Shalem et al., (2014) Science 343:84 PMID:24336571; Wang et al., (2014) Science 343:80 PMID:24336569), under appropriate conditions. SpCas9 is targeted to DNA loci by a 20 nt sequence in the RNA; which is immediately upstream of a required 5'NGG motif called the protospacer adjacent motif (PAM). This 20 nt gRNA sequence directs the SpCas9 protein to its complement in DNA target sequence. Any mismatches between the gRNA and target DNA in this region reduce the efficiency of cleavage. Single mismatches that occur distal to the PAM are somewhat tolerated (Hsu et al., Nat Biotechnol 31:827, PMID:23873081), but multiple mismatches lead to substantial reductions in the efficiency of cleavage. Thus; it is often desirable to configure gRNAs with targeting sequences that are perfectly complementary in their DNA targets and have at least 2 or 3 mismatches with all other 20mers in the genome.

For the targeted in vitro cleavage of DNA, gRNAs are usually prepared by cloning an oligonucleotide encoding the desired 20 nt targeting sequence into a plasmid vector containing the constant regions of the gRNA downstream of a T7 promoter. This plasmid can then be used to produce gRNA by performing an in vitro transcription reaction with T7 RNA polymerase. The resulting gRNA is then purified and complexed with Cas9 protein. Target DNA is added and the cleavage reaction is performed for ~1 hour at 37 degrees. Alternatively, gRNA can be produced by synthesizing a DNA oligonucleotide encoding the 20 nt targeting sequence and flanking constant regions and performing megaprimer PCR or stitching PCR to add the remaining constant portion of the gRNA and the T7 promoter. Often, it is desirable to cleave DNA at a large number of specific loci. One efficient way to achieve this is to synthesize hundreds or thousands of DNA oligonucleotides each encoding a different gRNA targeting sequences on a microarray (Singh-Gasson et al., (1999) Nat Biotechnol 17:974; Hughes et al.; (2001) Nat Biotechnol 19:342), This library can then be cloned into a plasmid containing the T7 promoter and gRNA constant region and gRNA produced as described above. Alternatively, the megaprimer or stitching PCR based strategies described previously can be used.

BRIEF DESCRIPTION OF THE FIGURES

FIG. 2 illustrates a cassette of the type described in co-pending PCT Application No. PCT/US2015/055833, hereinafter referred to as the '833 PCT, herein incorporated by reference in its entirety.

DETAILED DESCRIPTION OF SOME OF THE EMBODIMENTS

Figure 1:
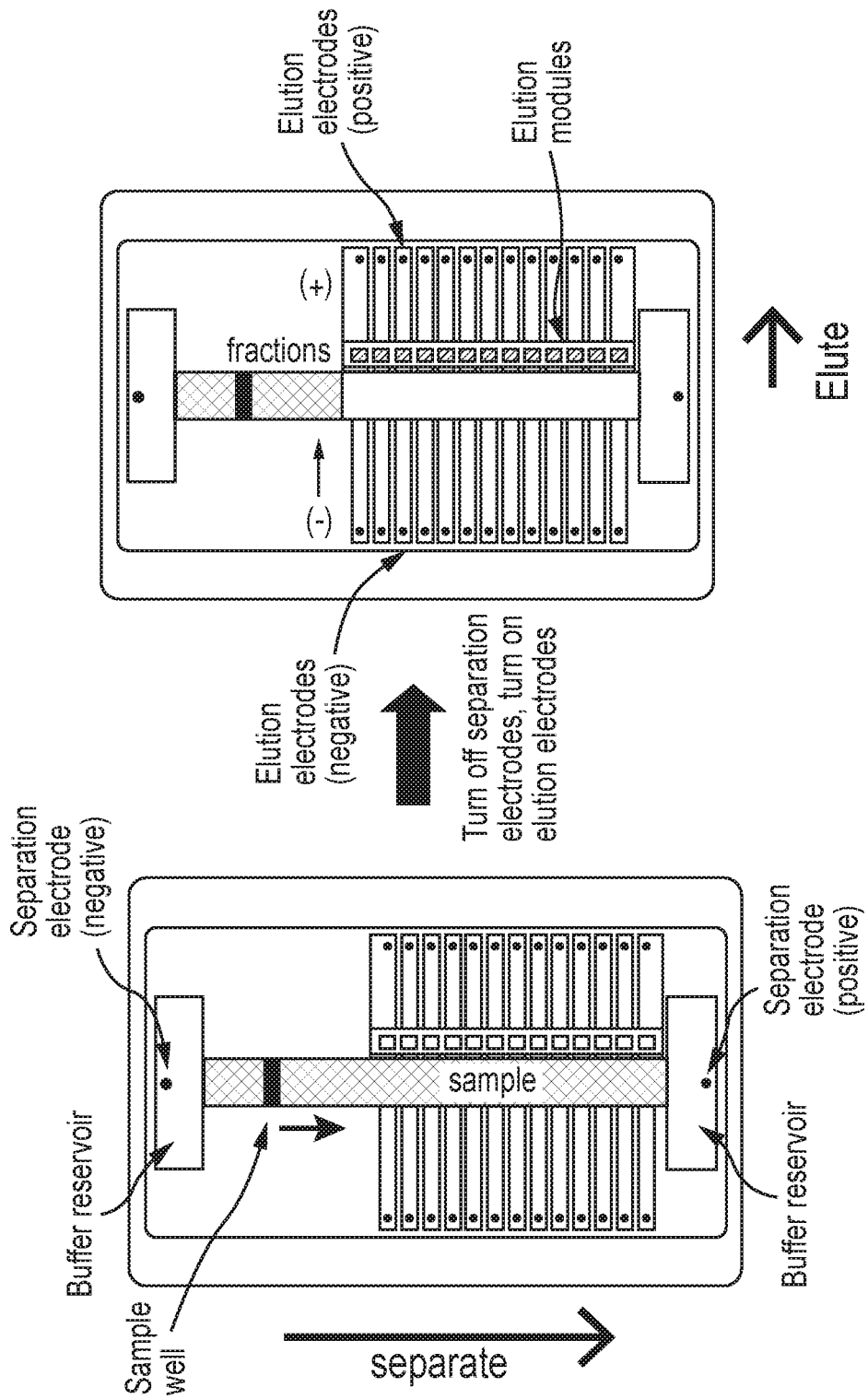
FIG. 1 illustrates a schematic view of a preparative electrophoresis cassette and size selection process as described in US Publication No. 2015/00101932, herein incorporated by reference in its entirety.

FIGS. 3A-E illustrates embodiments of the present disclosure which utilize a gel electrophoresis cassette (e.g., as illustrated in FIGS. 1 and 2). FIG. 1 shows a schematic view of a commercial preparative electrophoresis cassette and size selection process using that cassette. In the left side of FIG. 1, the sample nucleic acids are electrophoresed downward from a sample well through an agarose filled separation channel, where they are separated by size. After separation, the separation electrodes are turned off, and the elution electrodes are turn on, thereby electroeluting the separated nucleic acids sideways into a set of elution modules to the right of the separation channel. The eluted nucleic acids are in liquid electrophoresis buffer and can be removed from the elution modules using manual or automated pipetting means.

The cassette of FIG. 1 is modified, as shown in FIG. 2, to provide a cassette of the type described in the '833 PCT. In this cassette, a sample well is provided along with a reagent well upstream of the sample well (i.e., upstream corresponding to the side proximal to the negative separation electrode). In some embodiments, the reagent well is larger in volume than the sample well, and slightly wider and deeper than the sample well to ensure that the sample well is completely surrounded by the reagents from the reagent well during the electrophoretic purification step.

Figure 3:
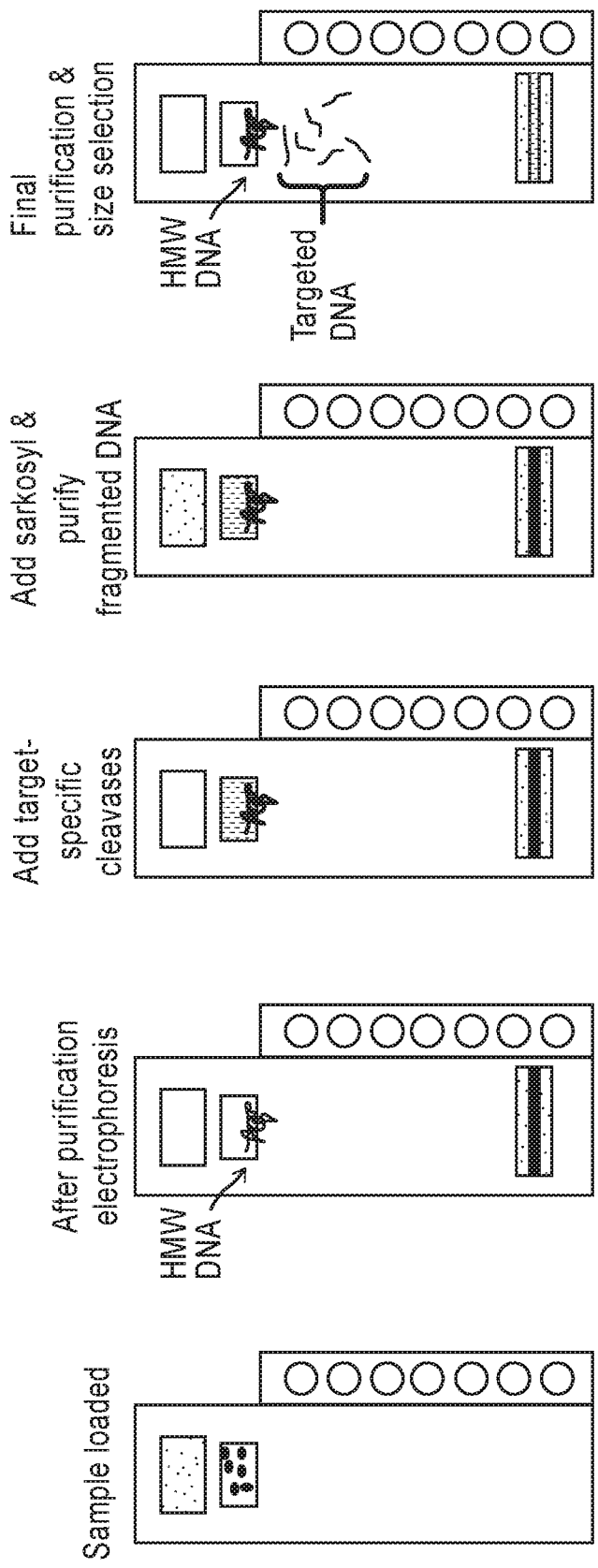
FIGS. 3A-E illustrate a schematic view of a system and method for obtaining targeted DNA fragments from HMW DNA according to some embodiments of the present disclosure.

The exemplary workflow, according to some embodiments of the disclosure, shown in FIGS. 3A-E, is as follows (for simplicity of illustration, only the separation channel and elution channels are shown in the figure). FIG. 3A shows the cassette immediately after sample loading. Preferably, the sample is a cell suspension. Examples of preferred samples can be any of whole blood, purified white blood cells, suspensions of cultured cells, suspensions of microorganisms, suspension of cells prepared from buccal swab, and samples prepared from solid tissues that have been enzymatically treated to disperse the tissue into a suspension of single cells. Preferably, the sample cell suspension is loaded in an isopycnic loading solution so that the cells will neither float nor sink during purification electrophoresis.

Also in FIG. 3A, a lysis reagent is loaded in the reagent well. In some embodiments, the reagent well and sample well are physically isolated and cannot mix during loading. In some embodiments, the lysis reagent comprises negatively charged components that can be electrophoresed through the gel matrix into the sample well where they will gently lyse the cells without any mixing or stirring of the sample well components. In this way, lysis occurs in a shear-free fashion, and very HMW DNA is generated. Preferred lysis reagents include anionic detergents such as SDS and sodium sarcosyl, and detergent-tolerant proteases, such as proteinase K, chelating agents such as EDTA and EGTA, and mixtures of the above.

After loading the sample and reagent wells, an electrophoretic field can be applied using separation electrodes. During the initial phases of electrophoresis, the lysis reagents are delivered to the sample well where cells are lysed rapidly and gently with little or no viscous shear flow. In some embodiments, proteins and other cellular components are denatured and/or degraded by the lysis reagents, and coated with negative charge by the anionic detergent in the lysis reagent. As a result, such contaminants are rapidly electrophoresed from the sample well. However, since cell lysis is quick and gentle, the cellular DNA remains largely undegraded, and is of such large size (estimated to be >10 megabases) that it will not electrophorese into the separation gel column. The end of the purification electrophoresis is shown schematically in FIG. 3B, with the HMW DNA trapped in the downstream wall of the sample well, and the detergent micelles and the detergent-protein complexes at the bottom of the gel.

Although the DNA becomes trapped in the gel matrix during this purification step, it is processable by DNA modification enzymes such as restriction enzymes, transposases, polymerases, and exonucleases as described in the '833 PCT. In FIG. 3C, the sample and reagent wells are emptied, the reagent well refilled with buffer that is compatible with CRISPR-Cas9 cleavage buffer (see example below), and the sample well is refilled with the custom CRISPR-Cas9 cleavage reagents that are configured to cleave at sequences that surround DNA regions of interest for downstream analyses, for instance, by DNA sequencing. The cassette is incubated at a suitable temperature for a suitable period of time to allow efficient cleavage of the HMW DNA. Preferably, the DNA fragments released by the customized CRISPR-Cas9 reagents are less than about 5 megabases in size, and more preferably, less than about 2 megabases in size, so that the released DNA can be reliably separated from the uncleaved DNA which remains trapped at the lip of the sample well.

In FIG. 3D, after cleavage of the sample DNA, the reagent well can be emptied and refilled with a purification reagent. In some embodiments, the purification reagent is similar to or identical to the lysis reagent. Separation electrodes can then be activated. Accordingly, the Cas9-gRNA complexes can then be denatured and/or degraded as the lysis reagent is electrophoresed through the sample well.

Although it is anticipated that the inventive method is particularly useful for long-range genomic analyses, the method can be applicable for targeted selection of both small ("small" here meaning from about 10 to about 5000 bp in length) and large ("large" here meaning from 5000 bp up to mid-single megabase pairs in length) DNA fragments. In either case, a pair customized CRISPR/Cas9 cleavage reagents is configured for each genomic DNA fragment to be recovered for analysis.

For some embodiments corresponding to samples comprising cells with cell walls (e.g., bacteria, fungi, and plants), the sample is loaded in an isotonic reagent mixture containing enzymes configured to digest the cell walls, thereby converting the original sample cells into spheroplasts. In some such embodiments, the sample well is loaded without adding lysis reagent to the reagent well, so that cell wall digestion can take place for an extended period, without the chance for diffusion of the lysis reagent into the sample well prior to the electrophoresis purification step.

The following examples are presented to help illustrate and support some of the embodiments of the present disclosure, and are not to be considered as limiting.

Example 1: Custom Cas9 gRNA Cleavase Reagents for Isolation of Long DNA Fragments from the HLA Locus Background HLA molecules are encoded by class I (HLA-A, -B, -C) and II (HLA-DRB1/3/4/5, -DQB1, -DPB1)

genes. These genes produce diverse peptides to T-cell receptors, which regulate T cell development, self-tolerance and adaptive immunity. HLA molecules are immunogenic and can become the target of cellular and humoral immune response in the allogeneic transplant setting, and so HLA typing has become the standard of care for assessing the immunological compatibility between a transplant donor and recipient. HLA typing at single-base resolution has been performed using Sanger sequencing, which is labor-intensive and costly. Due to the large number of single nucleotide variants (SNV) that need to be phased into separate haplotypes, cis-trans ambiguities frequently arise that can only be resolved by additional testing including PCR with sequence specific primers. Several next-generation sequencing (NGS) technologies, including Illumina and Ion-torrent, have lowered the cost of HLA typing, but they are unable to directly phase SNVs over distances greater than a few hundred base pairs. Third generation sequencers such as those produced by Pacific Biosciences (PacBio) and Oxford Nanopore can inexpensively obtain long reads from single DNA molecules. This may, in principle, allow haplotype-resolved sequencing of the HLA locus; however, there is currently no established methodology for selecting specific long DNA fragments from the genome. This can be accomplished by inventive methods of the present application. To do so the following steps are performed.

Oligonucleotides encoding gRNAs to cut long fragments from the HLA-A locus. DNA oligonucleotides encoding the targeting sequence of gRNAs and flanking bases are configured to cut the 5' and 3' ends of the HLA-A locus. One or more gRNAs can be targeted to each end (here, we target two). In this example, the targeting sequences and a small amount of constant gRNA sequence are ordered from IDT technologies and then cloned into the DR274 vector [PMID: 23360964], which encodes the constant region of the gRNA downstream of a T7 promoter. The resulting plasmid is PCR amplified and an in vitro transcription reaction is performed to produce gRNAs with the following sequences are produced:

```
5' ggNNNNNNNNNNNNNNNNNNNNGTTTTAGAGCTAGAAATAGCA
AGTTAAAATAAGGCTAGTCCGTTATCAACTTGAAAAAGTGGCACCG
AGTCGGTGCTTTTT,
``` where the "N"'s represent the gRNA targeting sequence, and the 2 g's that are 5' to these N's are required for T7 transcription start.

For example, to target the HLA-A gene, we use the following targeting sequences: For gRNAs 5' of HLA-A:
5HLA-A-TS1
5'-GAAAAGAACAGTTACGTAGC-3' (SEQ ID NO: 2), which is just upstream of a AGG PAM sequence and resides at chromosome 6 chr6:29,941,185-29,941,204 (all coordinates are from the human reference genome assembly version GRCh38).
5HLA-A-TS2
5'-CCAGAAGCTTCACAAGACCG-3' (SEQ ID NO: 3), which is just upstream of an AGG PAM and resides at chr6:29,941,096-29,941,115. Target sites 5HLA-A-TS1 and 5HLA-A-TS2 are configured to cleave genomic sites that flank the consensus HLA-A coding start (chr6:29,942,553) on the 5' side by approximately 1350 and 1440 bp, respectively.

3HLA-A-TS1
5'-ATTCCTTATATTCACCCCCA-3' (SEQ ID NO: 4) which is just upstream of a GGG PAM and resides at chr6:29949521-29949540
3HLA-A-TS2
5'-CATTCCTTATATTCACCCCC-3' (SEQ ID NO: 5) which is just upstream of an AGG PAM and resides at chr6: 29949520-29949539

3HLA-A-TS1 and 3HLA-A-TS2 overlap each other and are configured to cleave at a position that flanks the end of the HLA-A consensus coding region (chr6:29,945,453) on the 3' side by approximately 4090 bp.

Targeted Cas9 cleavage products from these HLA-A target sites are predicted to be approximately ~8330 bp (5HLA-A-TS1 to 2HLA-A-TS1 or 2) and 8420 bp (5HLA-A-TS2 to 3HLA-A-TS1 or 2) in length.

To clone each of these targeting sequences into the DR274 vector [PMID: 23360964], two primers are ordered for each targeting sequence and annealed together. These primers include some sequence from the constant portion of the gRNA or the flanking T7 promoter to facilitate cloning, and are as follows:

```
5HLA-A-TS1F
5'-TAGG GAAAAGAACAGTTACGTAGC-3

5HLA-A-TS1R
5'-AAAC GCTACGTAACTGTTCTTTTC-3

5HLA-A-TS2F
5'-TAGG TTGAAAGCAGCAGAATTCTT-3

5HLA-A-TS2R
5'-AAAC AAGAATTCTGCTGCTTTCAA-3

3HLA-A-TS1F
5'-TAGG ATTCCTTATATTCACCCCCA-3

3HLA-A-TS1R
5'-AAAC TGGGGGTGAATATAAGGAAT-3

3HLA-A-TS2F
5'-TAGG TCTATCAACAAATTGCTAGG-3

3HLA-A-TS2R
5'-AAAC CCTAGCAATTTGTTGATAGA-3
```

Cloning of gRNA encoding oligonucleotides into a vector with a T7 promoter. The plasmid vector DR274 is cut with BsaI, purified on an agarose gel, and the cleaned up using a Qiagen gel purification kit. 100 uM of each gRNA encoding oligonucleotide is annealed to its complement in the following reaction:

| | |
|---|---|
| ddH20 | 6 ul |
| 10X ligation buffer | 4 ul |
| each oligo | 5 ul |
| total | 20 ul |

This reaction is heated at 100° C. for 3-5 min. After, the heat block is turned off and allowed to cool. The annealed oligonucleotides are then phosphorylated using the following reaction:

| | |
|---|---|
| Annealed oligo | 1 ul |
| 10x ligation buffer | 1 ul |
| T4 polynucleotide kinase | 1 ul(10 unit) |
| ddH20 | 7 ul |
| Total | 10 ul |

This reaction is mixed by gentle vortexing and incubated at 37° C. for 30 min. Next, the annealed, phosphorylated, oligonucleotides are ligated into the plasmid encoding the T7 promoter using the following reaction:

| | |
|---|---|
| DR274 plasmid digested with Bsa1 | 1 ul |
| T4 DNA ligase | 1 ul |
| 10x T4 Ligation buffer | 2 ul |
| ddH20 | 16 ul |
| Total | 30 ul |

At 15° C. overnight, or room temperature 2 hours.

Next, 1 ul of the plasmid mix is transformed into *E. coli*, and plated on rich media (LB) agar plates supplemented with ampicillin. Amp' clones are selected, and plasmids containing desired guide RNA sequences are verified by colony PCR and Sanger sequencing. The correct clones are grown in 1 ml LB+amp liquid medium, overnight at 37° C. and plasmids are isolated from the cultures using a Qiagen DNA purification kit.

PCR amplification of gRNAs from plasmid template. To create the gRNAs from the plasmid template, the T7 promoter and gRNA region of the plasmid are amplified by PCR and then used as a template in an in vitro transcription reaction. The PCR primers are as follows: forward 4989 GTTGGAACCTCTTACGTGCC (SEQ ID NO: 30) rev 5008 AAAAGCACCGACTCGGTG (SEQ ID NO: 31). The PCR reaction is set up as follows:

| Component | Amount (per reaction) | Final amount/concentration |
|---|---|---|
| Phusion HF buffer | 5 μl | 0.5 x |
| Phusion GC buffer | 5 μl | 0.5 |
| 10 mM dNTP | 1 μl | 0.2 mM of each |
| forward 4989 25 μM | 1 μl | 0.5 μM |
| rev 5008 25 μM | 1 μl | 0.5 μM |
| gRNA encoding Plasmid digested with Dra1 | 1 μl | 50 ng |
| Phusion DNA Polymerase | 0.5 μl | 1 units |
| ddH2O | 35.5 μl | |
| TOTAL volume | 50 μl | |

This reaction is cycled as follows: 98° C. 30 s 1 cycle, (98° C., 10 s, 60° C. 30 s, 72° C. 30 s×35 cycles), 72° C. 5 min, 4° C. indefinitely.

This PCR will yield a 369 bp PCR fragment which is then purified with Qiagen column.

RNA synthesis reaction using Mmessage Mmachine T7 in vitro transcription kit (AMBION CAT #1344). To create gRNA from the DNA fragment, an in vitro transcription reaction is performed as follows:

| | |
|---|---|
| 10 x reaction buffer | 2 ul |
| 2x NTP/CAP | 10 ul |
| PCR product | 150 ng |
| Enzyme mix | 2 ul |
| Add H₂0 to 20 ul | |
| Incubate 4 hr at 37° C. | |

To recover the RNA, add 0.5 ul of Turbo DNAse (2 units/ul) and incubate 15 minutes at 37° C. Then add 30 ul of 50 mM EDTA pH 8.0. Heat to 80° C. for 15 minute to kill DNAse and recover the RNA using BIO-RAD Micro-Bio-spin Columns (cat #732-6250). Equilibrate the micro Bio-Spin P30 column in TE by filling with 500 ul of TE and spin 2 minutes at 1000 g. Then load 50 ul of sample onto column, spin 4 minutes at 1000 g. The sample will elute in ~50 ul. The gRNA should be at a concentration of approximately ~200 ng/ul for a total yield ~10 ug of RNA.

In vitro reconstitution of custom functional Cas9-gRNA complexes. To form active gRNA-Cas9 complexes, mix 2.5 ul of cas9 protein (3.18 ug/ul, New England Biolabs cat #M0386M (20 uM cas9 protein)) with 10 ul of RNA (2000 ng) in a total of 80 ul of 1×NEB buffer 4 (New England Biolabs, 50 mM Potassium Acetate, 20 mM Tris-acetate, 10 mM Mg-acetate, 1 mM DTT, pH 7.9). Pre-incubate at 37 for 15 minutes. The concentration of reconstituted cas9 is 0.63 uM (0.1 ug/ul).

Example 2. Targeted Excision and Recovery of Long DNA Fragments from the Human HLA Locus Using the Inventive Electrophoretic Method This example uses the preparative electrophoresis system described in the '833 PCT, an example of which is also shown in FIG. 2, right. A schematic workflow for this example is shown in FIGS. 3A-E, where only the separation gel and the elution modules are shown, for reasons of simplicity of illustration. An inventive cassette containing a 0.75% agarose in 0.5×KBB buffer (51 mM Tris (base), 29 mM TAPS (acid), 0.1 mM EDTA (acid), pH 8.7) is used. The total volumes of the reagent and sample wells were 350 and 90 ul, respectively.

Preparation of Human WBCs from whole blood by selective lysis of the RBCs. All steps are performed at room temperature. To 12 mL whole blood (ACD anticoagulant) add 36 mL Red Blood Cell (RBC) lysis buffer (155 mM ammonium chloride; 10 mM NaHCO₃; 1 mM Na₂EDTA) was added. The solution was rocked for 3 minutes and white cells pelleted by centrifugation 400×g for 4 minutes. The pink supernatant was decanted, and the red pellet resuspended by vortexing in 25 mL of RBC lysis buffer. After a second spin and decantation, the pink pellet was resuspended in 900 uL RBC lysis buffer.

Measurement of WBC DNA concentration by Qubit. A Qubit HS assay (Life Technologies) was used. WBCs were lysed by mixing 40 uL of WBCs with 160 uL of TE/50 mM NaCl/1% SDS, followed by incubation at 65° C. for 3 minutes. TE (800 uL) was added, and after vortexing to reduce viscosity, 1 or 2.5 uL of the DNA was added to 199 uL of Qubit reagent, per the vendor's protocol.

Targeted recovery of HLA fragments by custom-gRNA-Cas9 reagents and preparative electrophoresis. Purified WBCs (containing 10-12 ug of genomic DNA) were loaded into the empty sample well of the cassette in RBC lysis buffer. Total volume of the loaded sample was 80 ul. Lysis buffer (10 mM Tris-HCl, pH7.5, 1 mM EDTA, 3% SDS, 5% glycerol, 50 ug/mL each bromophenol blue and phenol red), 320 ul, was added to the empty reagent well. See FIG. 3A.

Cell lysis and DNA purification was carried out by electrophoresis in a SageELF instrument (Sage Science, Inc.) using the separation electrodes at 100V for 40 minutes. See FIG. 3B.

After purification electrophoresis, the reagent and sample wells were emptied. The reagent well was reloaded with 320 ul of 1×NEB buffer 4. The sample well was reloaded with 80 ul of 1×NEB buffer #4 containing the reconstituted custom Cas9-gRNA reagent mixture described in Example 1 at a concentration of 5 pM (total concentration of Cas9 protein) in a total volume of 80 ul. The cassette was incubated at 37 C for 60 minutes to allow cleavage of the HLA target sites within the immobilized genomic DNA. See FIG. 3C.

After cleavage, the reagent and sample wells were emptied, the reagent well was refilled with 320 ul 0.5×KBB+3% sodium sarcosyl. The sample well was filled with 80 ul of the same buffer, additionally containing 200 ug/ml proteinase K. The cassette was incubated at 37 C for 30 minutes to allow digestion of the Cas9 protein reagent (see FIG. 3D).

After digestion, the cassette was electrophoresed in a SageELF instrument in separation mode using a program of 60V continuous field for 1 hour. See FIG. 3E.

After separation electrophoresis, electroelution is carried out in the ELF instrument for 45 minutes using a voltage of 50V. At the end of elution, a 25V field is applied in the reverse direction for 5 seconds to help release the eluted DNA from the ultrafiltration membrane of the elution modules. The targeted fragments can be removed from the elution modules in electrophoresis buffer by manual or automated liquid handling means (Elution and recovery from elution modules not shown in FIGS. 3A-E).

Example 3: Custom gRNA-Cas9 Constructions for Targeted Isolation of Human Protein Coding Sequences (Exon Isolation)

Guide RNA design. We designed/configured gRNAs for cleaving all human exons (along with some flanking non-exon sequence on each side of the exon) into fragments 200-500 bp in length. gRNAs are picked by examining all 20 bp DNA sequences that are immediately 5' of an NGG site and then pairs that flank exons are chosen from this set. For exons longer than 500 base pairs, gRNAs are also configured internal to the exon so that the exon sequences are cut into 2 or more fragments less than 500 base pairs in length. gRNAs that have an exact match, or a 1 or 2 bp mismatch at an off-target genome site are discarded.

Massively Parallel Oligonucleotide Synthesis and Amplification. A library of gRNA encoding nucleotides was ordered from Custom Array (Bothell, Wash., USA). The format is 5'CGCTCGCACCGCTAGC<u>TAATACGACTCACTATAGG</u>NNNNNNNNN

NNNNNNNNNNNGTTTTAGAGCTAGAAATAGCAAGTTAAAATAAGGC

TAGTCCGTTATCAACTTGAAAAAGTGGCACCGAGTCGGTGCTTTTT, where the "N"'s represents the targeting sequence, and the underlined sequence is the T7 promoter. This library is amplified by performing PCR with the following primers:

```
forward:
5'CGCTCGCACCGCTAGCTAATACGACT-3',
and reverse
5'AAAAAGCACCGACTCGGTGCCACTTTT-3'.
```

The PCR product is expected to be 134 bp and is gel purified.

Production of gRNA by in vitro transcription using Mmessage Mmachine T7 (AMBION CAT #1344). To create gRNA from the DNA fragment, an in vitro translation reaction is performed as follows:

| | |
|---|---|
| 10 x reaction buffer | 2 ul |
| 2x NTP/CAP | 10 ul |
| Amplified library product | 150 ng |
| Enzyme mix | 2 ul |
| Add H$_2$0 to 20 ul | |
| Incubate 4 hr at 37° C. | |

To recover the RNA, add 0.5 ul of Turbo DNAse (2 units/ul) and incubate 15 minutes at 37° C. Then add 30 ul of 50 mM EDTA pH 8.0. Heat to 80° C. for 15 minute to kill DNAse and recover the RNA using BIO-RAD Micro-Bio-spin Columns (CAT #732-6250). Equilibrate the micro Bio-Spin P30 column in TE by filling with 500 ul of TE and spin 2 minutes at 1000 g. Then load 50 ul of sample onto column, spin 4 minutes at 1000 g. The sample will elute in ~50 ul. The gRNA library should be at a concentration of approximately ~200 ng/ul for a total yield ~10 ug of RNA.

In vitro reconstitution of custom functional Cas9-gRNA complexes. To cleave genomic DNA, mix 2.5 ul of cas9 protein (3.18 ug/ul, New England Biolabs cat #M0386M (20 uM cas9 protein)) with 10 ul of RNA (2000 ng) in a total of 80 ul of 1×NEB buffer 4 (New England Biolabs, 50 mM Potassium Acetate, 20 mM Tris-acetate, 10 mM Mg-acetate, 1 mM DTT, pH 7.9). Pre-incubate at 37 for 15 minutes. The concentration of reconstituted cas9 is 0.63 uM (0.1 ug/ul).

Targeted excision and purification of exon-containing gDNA by preparative electrophoresis. Purification of total genomic DNA from human WBC's was carried out as described in Example 2. Targeted excision was also carried out as described in Example 2 with the two exceptions:
  (1) The cleavage step utilized a higher concentration of reconstituted gRNA-Cas9 complexes: 80 ul of reconstituted gRNA-Cas9 complexes at a concentration of 0.63 uM, reflecting the 20,000-fold higher number of cleavages needed to excise all exon-containing DNA, relative to the 8 sites used for the HLA-A case in Example 2.
  (2) The preparative gel cassette utilized a 2% agarose gel (instead of the 0.75% gel used for example 2), for better size resolution of the expected 200-500 bp targets.

Example 4—Characterization of Translocation Breakpoints by Targeted Genomic DNA Sequencing Cytogenetic studies led to the discovery that specific chromosome rearrangements were associated with human tumors. The first reproducible chromosome abnormality in a specific human cancer was the Philadelphia chromosome associated with chronic myelogenous leukemia. Later molecular studies showed that this rearrangement led to a fusion protein that consisted of c-abl, the homologue of the v-abl oncogene and a gene called bcr (breakpoint cluster region). This bcr-abl fusion protein is oncogenic and is the target of the highly successful therapeutic called Gleevec.

There are now hundreds if not thousands of chromosomal translocations associated with various tumors. A common site of chromosome breakage occurs within the gene encoding anaplastic lymphoma kinase (ALK) that resides on chromosome 2p23. It is translocated to a variety of different chromosomes in many different tumors PMID: 23814043. However, it is most commonly rearranged in a subset of non-Hodgkin lymphomas, where a translocation involving ALK and the nucleophosmin (NPM1) gene on chromosome 5q35 is observed PMID: 25869285. This translocation allows the formation of a NPM1-ALK fusion gene that is the target of the therapeutic crizotinib [PMID: 24491302]. The precise site of breakage in these translocations can be variable and therefore difficult to detect by conventional NGS. The ability to obtain a large DNA fragment containing the rearranged locus for sequence analysis would reduce the need for laborious cytogenetic assays.

Oligonucleotides encoding gRNAs to cut long fragments encompassing the NPM1-ALK translocation. To isolate this fragment, DNA oligonucleotides encoding gRNAs are configured to cut 5' of the NPM1 gene on chromosome 5q35 and 3' to the ALK gene on chromosome 2p23. In cells with the NPM1-ALK t(2;5) translocation, these gRNAs will direct Cas9 to cut a large fragment containing the rearranged junction. Two or more gRNAs can be targeted to each end to insure cutting at the designated region and excision of the NPM1-ALK containing fragment.

Short oligonucleotides encoding the targeting sequence are cloned into the DR274 vector [PMID: 23360964] that encodes the constant region of the gRNA downstream of the T7 promoter. After in vitro transcription, gRNAs with the following sequence are produced: After in vitro transcription, gRNAs with the following sequence are produced:

```
5' ggNNNNNNNNNNNNNNNNNNNNNGTTTTAGAGCTAGAAATAGCA
AGTTAAAATAAGGCTAGTCCGTTATCAACTTGAAAAAGTGGCACCG
AGTCGGTGCTTTTT,
``` where the "N"'s represent the gRNA targeting sequence, and the 5' g's are required for T7 transcription.

In this example, we use the following targeting sequences:
For gRNAs 5' side of NPM1:
NPM1-TS1
5' CAAGTCACCCGCTTTCTTTC 3' (SEQ ID NO: 18), which is just upstream of a AGG PAM sequence and resides at chr5:171,387,031-171,387,050, which is approximately 900 bp upstream of the start of the NPM1 coding sequence (chr5: 171,387,949), and is about 4750 bp upstream of the start of 910 bp-long NPM1 intron 5 (chr5: 171,391,799), where many NPM1-ALK breakpoints occur.
NPM1-TS2
5'GACTTTGGAGATGTTTCTC3' (SEQ ID NO: 19) which is just upstream of an AGG PAM and resides at chr5:171,387,185-171,387,204, which is approximately 750 bp upstream of the start of the NPM1 coding sequence, and ~4600 bp upstream of the start of NPM1 intron 5.

For gRNA's on the 3' side of ALK:
ALK-TS1
5'-GAAGAAAACATGGCACAAAT-3' (SEQ ID NO: 20) which is just upstream of a GGG PAM and resides at chr2: 29,190,272-29,190,291, which is 2930 bp downstream (3') from the end of the ALK coding sequence (chr2: 29,193, 225), and 33240 bp downstream (3') from the end of the 1940-bp-long ALK intron 19, where many NPM1-ALK breakpoints occur.
ALK-TS2
5'-CAATGGGTCAGATAACTCAA-3' (SEQ ID NO: 21) which is just upstream of a GGG PAM and resides at chr2: 29,190,518-29,190,537, which is ~2700 bp downstream (3') from the end of the ALK coding sequence.

Figure 4:
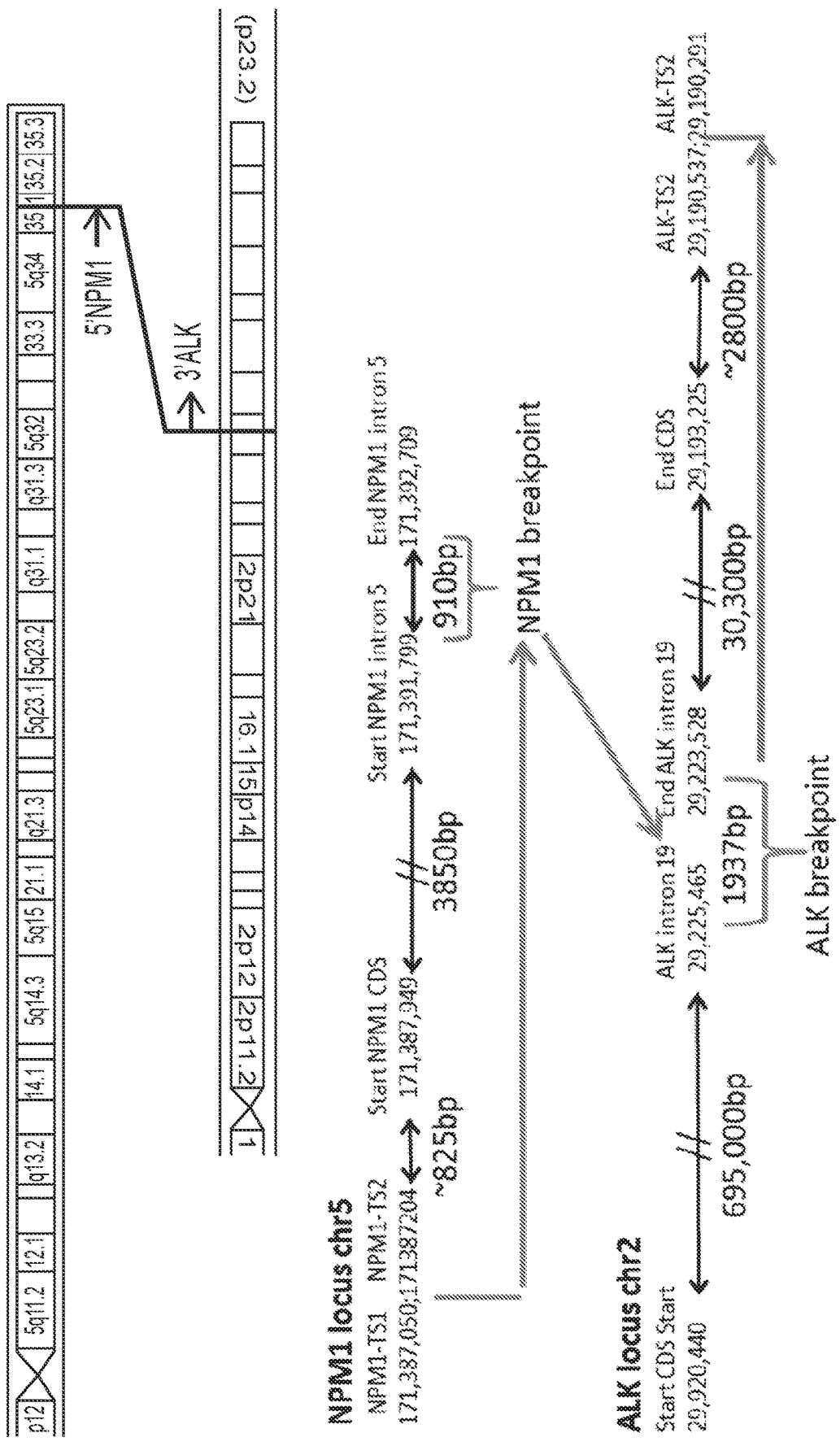
FIG. 4 illustrates a schematic diagram of targeting sites, the relevant coding regions, and some common breakpoints giving rise to the NPM1-ALK fusion rearrangement.

FIG. 4, shows a schematic diagram of the targeting sites, the relevant coding regions, and some common breakpoints giving rise to the NPM1-ALK fusion rearrangement (Morris, et al., (1994) Science 263:1281; Duyster, et al, (2001) Oncogene 20:5623).

Taking into consideration the possible variation in fragment size due the alternative gRNA target sites on either end of the fusion, and also the variation in the position of translocation breakpoints within the 910 bp NPM1 intron 5 and 1940 bp ALK intron 19, digestion of NMP1-ALK fusion genes with the custom gRNA-Cas9 complexes described above should produce fragments between 37.5 kb and 40.8 kb in length.

To clone each of these targeting sequences into the DR274 vector two primers are ordered for each targeting sequence and annealed together. These primers include some sequence from the constant portion of the gRNA or the flanking T7 promoter to facilitate cloning, and are as follows:

NPM1-TS1F
5'-TAGGCAAGTCACCCGCTTTCTTTC-3

NPM1-TS1R
5'-AAACGAAAGAAAGCGGGTGACTTG-3

NPM1-TS2F
5'-TAGGACTTTGGAGATGTTTTCTC-3

NPM1-TS2R
5'-AAACGAGAAAACATCTCCAAAGT-3

ALK-TS1F
5'-TAGGAGGGGCGCCCAATTTTGTCT-3

ALK-TS1R
5'-AAACAGACAAAATTGGGCGCCCCT-3

ALK-TS2F
5'-TAGGTCTATCAACAAATTGCTAGGAGG-3

ALK-TS2R
5'-AAAC CCTAGCAATTTGTTGATAGA-3

Cloning of gRNA encoding oligonucleotides into a vector with a T7 promoter. The plasmid vector DR274 [ref] is cut with BsaI, purified on an agarose gel, and the cleaned up using a Qiagen gel purification kit. 100 uM of each gRNA encoding oligonucleotide is annealed to its complement in the following reaction:

| | |
|---|---|
| ddH20 | 6 ul |
| 10X ligation buffer | 4 ul |
| each oligo | 5 ul |
| total | 20 ul |

This reaction is heated at 100° C. for 3-5 min. After, the heat block is turned off and allowed to cool. The annealed oligonucleotides are then phosphorylated using the following reaction:

| | |
|---|---|
| Annealed oligo | 1 ul |
| 10x ligation buffer | 1 ul |
| T4 polynucleotide kinase | 1 ul(10 unit) |
| ddH20 | 7 ul |
| Total | 10 ul |

This reaction is mixed by gentle vortexing and incubated at 37° C. for 30 min.

Next, the annealed, phosphorylated, oligonucleotides are ligated into the plasmid encoding the T7 promoter using the following reaction:

| | |
|---|---|
| DR274 plasmid digested with Bsa1 | 1 ul |
| T4 DNA ligase | 1 ul |
| 10x T4 Ligation buffer | 2 ul |
| ddH20 | 16 ul |
| Total | 30 ul |

At 15° C. overnight, or room temperature 2 hours.

Next, 1 ul of the plasmid mix is transformed into *E. coli*, and plated on rich media (LB) agar plates supplemented with ampicillin. Amp$^r$ clones are selected, and plasmids containing desired guide RNA sequences are verified by colony PCR and Sanger sequencing. The correct clones are grown in 1 ml LB+amp liquid medium, overnight at 37° C. and plasmids are isolated from the cultures using a Qiagen DNA purification kit.

PCR amplification of gRNAs from plasmid template. To create the gRNAs from the plasmid template, the T7 promoter and gRNA region of the plasmid are amplified by PCR and then used as a template in an in vitro transcription reaction. The PCR primers are as follows: forward 4989 GTTGGAACCTCTTACGTGCC (SEQ ID NO: 30), rev 5008 AAAAGCACCGACTCGGTG (SEQ ID NO: 31). The PCR reaction is set up as follows:

| Component | Amount (per reaction) | Final amount/concentration |
|---|---|---|
| Phusion HF buffer | 5 μl | 0.5 x |
| Phusion GC buffer | 5 μl | 0.5 |
| 10 mM dNTP | 1 μl | 0.2 mM of each |
| forward 4989 25 μM | 1 μl | 0.5 μM |
| rev 5008 25 μM | 1 μl | 0.5 μM |
| gRNA encoding Plasmid digested with Dra1 | 1 μl | 50 ng |
| Phusion DNA Polymerase | 0.5 μl | 1 units |
| ddH2O | 35.5 μl | |
| TOTAL volume | 50 μl | |

This reaction is cycled as follows: 98° C. 30 s 1 cycle, (98° C., 10 s, 60° C. 30 s, 72° C. 30 s×35 cycles), 72° C. 5 min, 4° C. indefinitely. This PCR will yield a 369 bp PCR fragment which is then purified with Qiagen column.

RNA synthesis reaction using Mmessage Mmachine T7 in vitro transcription kit (AMBION CAT #1344). To create gRNA from the DNA fragment, an in vitro transcription reaction is performed as follows:

| | |
|---|---|
| 10 x reaction buffer | 2 ul |
| 2x NTP/CAP | 10 ul |
| PCR product | 150 ng |
| Enzyme mix | 2 ul |
| Add H$_2$0 to | 20 ul |
| Incubate 4 hr at 37° C. | |

To recover the RNA, add 0.5 ul of Turbo DNAse (2 units/ul) and incubate 15 minutes at 37° C. Then add 30 ul of 50 mM EDTA pH 8.0. Heat to 80° C. for 15 minute to kill DNAse and recover the RNA using BIO-RAD Micro-Biospin Columns (caT #732-6250). Equilibrate the micro Bio-Spin P30 column in TE by filling with 500 ul of TE and spin 2 minutes at 1000 g. Then load 50 ul of sample onto column, spin 4 minutes at 1000 g. The sample will elute in ~50 ul. The gRNA should be at a concentration of approximately ~200 ng/ul for a total yield ~10 ug of RNA.

In vitro reconstitution of custom functional Cas9-gRNA complexes. To form active gRNA-Cas9 complexes, mix 2.5 ul of cas9 protein (3.18 ug/ul, New England Biolabs cat #M0386M (20 uM cas9 protein)) with 10 ul of RNA (2000 ng) in a total of 80 ul of 1×NEB buffer 4 (New England Biolabs, 50 mM Potassium Acetate, 20 mM Tris-acetate, 10 mM Mg-acetate, 1 mM DTT, pH 7.9). Pre-incubate at 37 for 15 minutes. The concentration of reconstituted cas9 is 0.63 uM (0.1 ug/ul).

Targeted excision and purification of genomic NPM1-ALK fusion fragments by preparative electrophoresis. Purification of total genomic DNA from human WBC's was carried out as described in Example 2. Targeted excision using the NPM1-ALK translocation-specific Cas9 targeting complexes were also carried out as described in Example 2.

After digestion, the cassette was electrophoresed in a SageELF instrument in separation mode using a program of 60V continuous field for 1 hour, followed by a 2 hour period of pulsed-field electrophoresis at 80V using the waveform for resolving 5-430 kb DNA described in the Pippin Pulse User Manual (http://www.sagescience.com/product-support/pippin-pulse-support/).

After separation electrophoresis, electroelution is carried out in the ELF instrument for 45 minutes using a voltage of 50V. At the end of elution, a 25V field is applied in the reverse direction for 5 seconds to help release the eluted DNA from the ultrafiltration membrane of the elution modules. The targeted fragments can be removed from the elution modules in electrophoresis buffer by manual or automated liquid handling means (Elution and recovery from elution modules not shown in FIGS. 3A-E).

Any and all references to publications or other documents, including but not limited to, patents, patent applications, articles, webpages, books, etc., presented anywhere in the present application, are herein incorporated by reference in their entirety.

As noted elsewhere, the disclosed embodiments have been presented for illustrative purposes only and are not limiting. Other embodiments are possible and are covered by the disclosure, which will be apparent from the teachings contained herein. Thus, the breadth and scope of the disclosure should not be limited by any of the above-described embodiments but should be defined only in accordance with claims supported by the present disclosure and their equivalents. Moreover, embodiments of the subject disclosure may include methods, compositions, systems and apparatuses/devices which may further include any and all elements from any other disclosed methods, compositions, systems, and devices, including any and all elements corresponding to isolating nucleic acid from a biological sample (e.g., containing nucleic acid and non-nucleic acid elements). In other words, elements from one or another disclosed embodiments may be interchangeable with elements from other disclosed embodiments. Moreover, some further embodiments may be realized by combining one and/or another feature disclosed herein with methods, compositions, systems and devices, and one or more features thereof, disclosed in materials incorporated by reference. In addition, one or more features/elements of disclosed embodiments may be removed and still result in patentable subject matter (and thus, resulting in yet more embodiments of the subject disclosure). Furthermore, some embodiments correspond to methods, compositions, systems, and devices which specifically lack one and/or another element, structure, and/or steps (as applicable), as compared to teachings of the prior art, and therefore represent patentable subject matter and are distinguishable therefrom (i.e. claims directed to such embodiments may contain negative limitations to note the lack of one or more features prior art teachings).

When describing the nucleic acid processing, terms such as linked, bound, connect, attach, interact, and so forth should be understood as referring to linkages that result in the joining of the elements being referred to, whether such joining is permanent or potentially reversible. These terms should not be read as requiring the formation of covalent bonds, although covalent-type bond might be formed.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of" "only one of" or "exactly one of" "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

We claim:

1. A method for isolating fragments of genomic DNA regions of interest using an electrophoretic cassette comprising:

loading a sample containing particles having high-molecular-weight (HMW) DNA in a first well of a gel matrix of an electrophoresis cassette;

loading a lysis reagent into a second well of the gel matrix of the electrophoresis cassette;

applying an electrophoretic field to the gel matrix such that:

the lysis reagent is delivered to the first well so as to lyse the particles and release the HMW DNA from the particles;

cellular components are electrophoresed from the first well, and the HMW DNA is removed from the particles and trapped in a wall of the fist well;

emptying and refilling the first well with a custom CRISPR-Cas9 cleavage reagent configured to cleave at specific DNA sequences within the HMW DNA so as to liberate defined segments of the DNA as fragments of reduced size;

subjecting the gel matrix to an electrophoretic field, the field being configured to move and thereby separate the DNA fragments from uncleaved DNA of the HMW DNA which remains substantially immobile; and isolating the electrophoretically separated DNA fragments from the gel matrix.

2. The method of claim 1, wherein emptying and refilling additionally comprises emptying and refilling the second well with the CRISPR-Cas9 cleavage reagent.

3. The method of claim 1, wherein isolating the electrophoretically separated DNA fragments is by electroelusion.

4. The method of claim 1, wherein the uncleaved remainder of the HMW DNA remains entrapped in the gel matrix.

5. The method of claim 1, wherein the particles are contained in a liquid suspension and comprise at least one of intact cells selected from the group consisting of: animal, plant, bacterial, fungal, archebacterial, protozoan, and intact virus particles.

6. The method of claim 1, wherein the gel matrix comprises an agarose hydrogel at a concentration between 0.2% and 5% (weight/volume).

7. The method of claim 1, wherein the lysis reagent comprises an anionic detergent at a concentration between 0.05% and 10%.

8. The method of claim 7, wherein the anionic detergent is sodium dodecyl sulfate (SDS).

9. The method of claim 1, wherein the size of the HMW DNA is >10 megabase pairs in length, and the size of the DNA fragments is <2 megabase pairs in length.

10. The method of claim 1, wherein the particles are contained in a liquid suspension and comprise bacteria, plant, or fungal cells, and wherein the method further comprises subjecting the gel matrix to other enzymatic reagent treatments configured to remove the cell walls prior to exposing the gel matrix with the entrapped sample to the lysis reagent.

11. The method of claim 1, wherein the DNA fragments are isolated from the gel matrix by electroelution into an elution module containing liquid buffer.

12. A method for isolating fragments of genomic DNA regions of interest using an electrophoresis cassette comprising:

loading a sample containing particles having high-molecular-weight (HMW) DNA in a first well of a gel matrix of an electrophoresis cassette;

loading a lysis reagent into a second well of the gel matrix of the cassette;

applying an electrophoretic field to the gel matrix such that:
  the lysis reagent is delivered to the first cavity so as to lyse the particles and release the HMW DNA from the particles;
  cellular components are electrophoresed from the first well; and
  the HMW DNA are removed from the particles and trapped in a wall of the first well;

emptying and refilling the first well with a custom CRISPR-Cas9 cleavage reagent configured to cleave at specific DNA sequences within the HMW DNA so as to liberate defined segments of the DNA as fragments of reduced size;

incubating the cassette at a suitable temperature for a suitable period of time to allow efficient cleavage of the HMW DNA;

applying an electric field to the matrix so that digested DNA fragments are electrophoresed into the matrix and separated according to their size; and isolating the electrophoretically separated DNA fragments from the gel matrix.

* * * * *